(12) United States Patent
Cournoyer et al.

(10) Patent No.: US 7,214,699 B2
(45) Date of Patent: May 8, 2007

(54) INDAZOLE DERIVATIVES AS CRF ANTAGONISTS

(75) Inventors: Richard Leo Cournoyer, San Francisco, CA (US); David Garrett Loughhead, Belmont, CA (US); Counde O'Yang, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 388 days.

(21) Appl. No.: 10/724,971

(22) Filed: Dec. 1, 2003

(65) Prior Publication Data
US 2004/0110815 A1 Jun. 10, 2004

Related U.S. Application Data

(60) Provisional application No. 60/430,168, filed on Dec. 2, 2002.

(51) Int. Cl.
*A61K 31/416* (2006.01)
*C07D 231/56* (2006.01)

(52) U.S. Cl. .................. 514/403; 514/405; 548/362.1; 548/361.1; 548/362.5

(58) Field of Classification Search ............. 548/362.1, 548/361.1, 362.5; 514/403, 405
See application file for complete search history.

(56) References Cited

U.S. PATENT DOCUMENTS

| | | | |
|---|---|---|---|
| 5,668,145 A | 9/1997 | Bright | |
| 5,705,646 A | 1/1998 | Bright et al. | |
| 5,712,303 A | 1/1998 | Faraci et al. | |
| 5,760,225 A | 6/1998 | Yuan | |
| 6,005,109 A | 12/1999 | Faraci et al. | |
| 6,200,979 B1 | 3/2001 | Bright et al. | |
| 6,897,231 B2 * | 5/2005 | Bhagwat et al. | 514/403 |
| 6,914,062 B2 * | 7/2005 | Hayama et al. | 514/249 |
| 2004/0167127 A1 * | 8/2004 | Steffan et al. | 514/227.8 |

FOREIGN PATENT DOCUMENTS

| | | |
|---|---|---|
| WO | WO99/23077 A1 | 5/1999 |
| WO | WO 00/27394 A1 | 5/2000 |
| WO | WO 01/58869 A2 | 8/2001 |
| WO | WO-2002/002550 A1 * | 1/2002 |
| WO | WO 02/16348 A1 | 2/2002 |
| WO | WO 03/035625 A1 | 5/2003 |
| WO | WO 03/078403 A1 | 9/2003 |

OTHER PUBLICATIONS

Grigoriadis, Dimitri E., et al., "The CRF Receptor: Structure, Function and Potential for Therapeutic Intervention," *Curr. Med. Chem. —Central Nervous System Agents*, 2001, pp. 63-97, vol. 1, No. 1, Bentham Science Publishers Ltd.

Saito, et al., "Electrochemical formation of indazoles from tropone tosylhydrazones: electrochemical oxidations of sodium salts of tosylhydrazones of tropone and 2-phenyltropone," Heterocycles, (1992) pp. 129-134, vol. 34:1.

* cited by examiner

*Primary Examiner*—Laura L. Stockton
(74) *Attorney, Agent, or Firm*—Brian L. Buckwalter

(57) ABSTRACT

This invention relates to compounds which are generally CRF-1 receptor antagonists and which are represented by Formula I or Formula II:

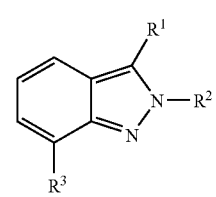

(I)

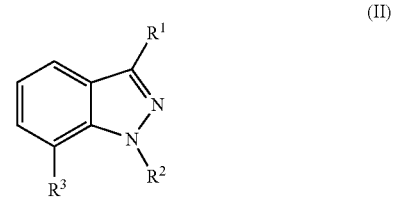

(II)

wherein $R^3$ is optionally substituted aryl or heteroaryl, $R^1$ and $R^2$ are as defined in the specification; or individual isomers, racemic or non-racemic mixtures of isomers, or pharmaceutically acceptable salts thereof. The invention further relates to processes for preparing such compounds, to pharmaceutical compositions containing such compounds, and to methods for their use as therapeutic agents.

45 Claims, No Drawings

INDAZOLE DERIVATIVES AS CRF ANTAGONISTS

CROSS REFERENCE TO PRIOR APPLICATIONS

This application claims benefit under Title 35 U.S.C. 119(e) of U.S. Provisional Application No. 60/430,168, filed Dec. 2, 2002, which is hereby incorporated by reference in its entirety.

FIELD OF THE INVENTION

This invention relates indazole derivatives of formula I and II with CRF activity, and associated pharmaceutical compositions, and methods for use as therapeutic agents.

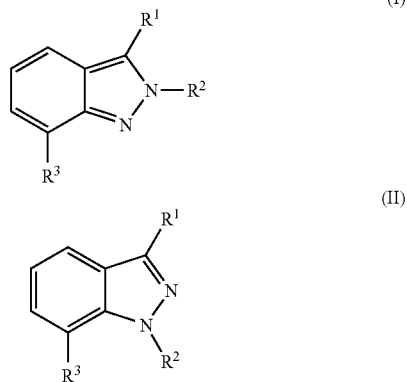

BACKGROUND OF THE INVENTION

Corticotropin releasing factor (CRF) or hormone (CRH) is one of several neurohormones synthesized by specific hypothalamic nuclei in the brain where it activates the transcription of the pro-opiomelanocortin (POMC) gene resulting in release of adrenocorticotropic hormone (ACTH) and beta-endorphin from anterior pituitary cells (Vale et al, *Science* 213, 1394–1397 (1981)). The fundamental role of CRF is to prepare the organism for an appropriate response to various stressors such as physical trauma, insults of the immune system and social interactions. CRF also has CNS effects by acting at higher centers in the brain, particularly cortical regions where there is a widespread distribution of CRF neurons. CRF is believed to be a key intermediary in communication between the immune, central nervous, endocrine and cardiovascular systems (Sapolsky et al, *Science* 238, 522–524 (1987)). The role played by CRF in integrating the response of the immune system to physiological, psychological and immunological stressors has been described in the art, e.g. J. E. Blalock, Physiological Reviews 69, 1 (1989) and J. E. Morley, *Life Sci.* 41, 527 (1987).

CRF antagonists are effective in the treatment of a wide range of stress-related illnesses, mood disorders such as depression, major depressive disorder, single episode depression, recurrent depression, child abuse induced depression, postpartum depression, dysthemia, bipolar disorder and cyclothymia; chronic fatigue syndrome; eating disorders such as obesity, anorexia and bulimia nervosa; generalized anxiety disorder; panic disorder; phobias; obsessive-compulsive disorder; post-traumatic stress disorder; pain perception such as fibromyalgia; headache; stress-induced gastrointestinal dysfunction such as irritable bowel syndrome (IBS), colonic hypersensitivity or spastic colon; hemorrhagic stress; ulcers; stress-induced psychotic episodes; inflammatory disorders such as rheumatoid arthritis and osteoarthritis; asthma; psoriasis; allergies; premature birth; hypertension; congestive heart failure; sleep disorders; neurodegenerative diseases such as Alzheimer's disease, senile dementia, Parkinson's disease and Huntington's disease; head or spinal cord trauma; ischemic neuronal damage; excitotoxic neuronal damage; epilepsy; stroke; psychosocial dwarfism; chemical dependencies and addictions; drug and alcohol withdrawal symptoms; stress-induced immune dysfunctions; immune suppression and stress-induced infections; cardiovascular or heart related diseases; fertility problems; and/or human immunodeficiency virus infections. Accordingly clinical data suggests that CRF receptor antagonists may represent novel antidepressants and/or anxiolytic drugs that may be useful in the treatment of the neuropsychiatric disorders manifesting hypersecretion of CRF.

In view of the above, efficacious and specific antagonists of CRF are desired as potentially valuable therapeutic agents for the treatment of psychiatric disorders and neurological diseases. It is thus desirable to discover new CRF antagonists.

Published PCT application WO 02/16348 (L. Hennequin) describes indazole derivatives which are inhibitors of vascular endothelial growth factor. Published PCT application WO 01/58869 A2 (K. Leftheris et al.) discloses indazole derivatives which are cannabinoid receptor modulators.

DETAILED DESCRIPTION OF THE INVENTION

This invention relates to compounds comprising Formula I

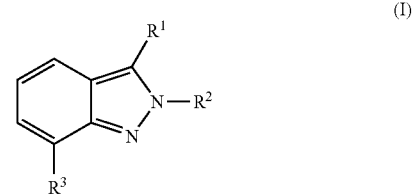

wherein:
$R^1$ is $-NR^aR^b$, $-CR^cR^dR^e$, $CO_2R^a$, or $-C(O)NR^aR^b$; or $R^1$ is hydrogen, cycloalkenyl, aryl, or heteroaryl, where each aryl or heteroaryl is optionally substituted with one or more substituents independently selected from $C_{1-6}$ alkyl, $C_{1-6}$ alkoxy, $C_{1-6}$ alkylthio, $C_{1-6}$ alkylsulfonyl, halogen, haloalkyl, cyano, nitro, $-C(O)NR^{a'}R^{b'}$, and $-NR^{a'}R^{b'}$, where $R^{a'}$ and $R^{b'}$ are each independently selected from the group consisting of hydrogen, $C_{1-9}$ alkyl, and $C_{1-9}$ alkylcarbonyl;

$R^2$ is hydrogen, $C_{1-6}$ alkyl, $C_{3-6}$ cycloalkyl, $C_{3-6}$ cycloalkyl-$C_{1-3}$ alkyl, $C_{1-6}$ alkylcarbonyl, $C_{1-6}$ alkylsulfonyl, aryl, or arylalkyl, wherein said aryl or arylalkyl is optionally substituted with one or more substituents independently selected from $C_{1-6}$ alkyl, haloalkyl, $C_{1-6}$ alkoxy, and halogen;

$R^3$ is aryl or heteroaryl, each optionally substituted with one or more substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —NR$^{a''}$R$^{b''}$, where R$^{a''}$ and R$^{b''}$ are each independently selected from the group consisting of hydrogen, $C_{1-9}$ alkyl, and $C_{1-9}$ alkylcarbonyl;

R$^a$ and R$^b$ (i) taken independently are each selected from the group consisting of hydrogen, $C_{1-9}$ alkyl, hydroxyalkyl, $C_{1-6}$ alkoxyalkyl, $C_{1-6}$ alkylthioalkyl, carboxyalkyl, acyl, $C_{3-6}$ cycloalkyl, $C_{3-6}$ cycloalkyl-$C_{1-3}$ alkyl, di-$C_{3-6}$ cycloalkyl-$C_{1-3}$ alkyl, $C_{1-6}$ heteroalkyl, aminoalkyl, aminocarbonylalkyl, cyanoalkyl, $C_{5-8}$ heterocyclyl, heterocyclylalkyl, aryl, arylalkyl, heteroaryl, heteroarylalkyl, phenylalkyl, diphenylalkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or (ii) taken together, along with the nitrogen atom to which they are attached, are a heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$ alkyl, haloalkyl, $C_{1-6}$ alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group;

R$^c$ is hydrogen, hydroxy, $C_{1-6}$ alkoxy, or —NR$^{a'''}$R$^{b'''}$;

R$^d$ and R$^e$ are each independently selected from the group consisting of hydrogen, $C_{1-9}$ alkyl, hydroxyalkyl, $C_{1-6}$ alkoxyalkyl, $C_{1-6}$ alkylthioalkyl, heteroalkyl, heterocyclyl, heterocyclylalkyl, $C_{3-6}$ cycloalkyl, $C_{3-6}$ cycloalkyl-$C_{1-3}$ alkyl, di-$C_{3-6}$ cycloalkyl-$C_{1-3}$ alkyl, aryl, arylalkyl, heteroaryl, heteroarylalkyl, phenylalkyl, diphenyl-$C_{1-3}$alkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, and halogen; or R$^c$ and R$^d$ are taken together to form a divalent group selected from $C_{1-6}$ alkylidenyl, $C_{1-6}$ heteroalkylidenyl, $C_{3-6}$ cycloalkylidenyl, $C_{3-6}$ cycloalkyl-alkylidenyl, $C_{3-6}$ cycloalkyl-$C_{1-3}$ alkyl-alkylidenyl, $C_{3-6}$ heterocyclylidenyl, $C_{3-6}$ heterocyclyl-$C_{1-3}$ alkylidenyl, $C_{3-6}$ heterocyclylalkyl-$C_{1-3}$ alkylidenyl, aryl-$C_{1-3}$ alkylidenyl, aryl-$C_{1-3}$alkyl-alkylidenyl, heteroaryl-$C_{1-3}$alkylidenyl, and heteroarylalkyl-$C_{1-3}$ alkylidenyl, wherein each of said cycloalkyl, aryl, or heteroaryl groups is optionally substituted with one or more substituents independently selected from $C_{1-6}$ alkyl, haloalkyl, $C_{1-6}$ alkoxy, amino, alkylamino, dialkylamino, and halogen; or R$^d$ and R$^e$ are taken together with the carbon to which they are attached to form a cycloalkyl or heterocyclyl ring;

R$^{a'''}$ and R$^{b'''}$ (i) are each independently selected from the group consisting of hydrogen, $C_{1-9}$ alkyl, hydroxyalkyl, $C_{1-6}$ alkoxyalkyl, $C_{1-6}$ alkylthioalkyl, carboxyalkyl, acyl, $C_{3-6}$ cycloalkyl, $C_{3-6}$ cycloalkyl-$C_{1-3}$ alkyl, di-$C_{3-6}$ cycloalkyl-$C_{1-3}$ alkyl, $C_{1-6}$ heteroalkyl, aminoalkyl, aminocarbonylalkyl, cyanoalkyl, $C_{5-8}$ heterocyclyl, heterocyclylalkyl, aryl, arylalkyl, heteroaryl, heteroarylalkyl, phenylalkyl, diphenyl-$C_{1-3}$ alkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or (ii) are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$ alkyl, haloalkyl, $C_{1-6}$ alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group;

or individual isomers, racemic or non-racemic mixtures of isomers, or pharmaceutically acceptable salts thereof; or, a compound of Formula II

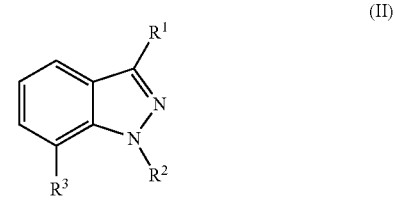

(II)

wherein:

R$^1$ is —NR$^a$R$^b$, —CR$^c$R$^d$R$^e$, CO$_2$R$^a$; or R$^1$ is hydrogen, cycloalkenyl, aryl, or heteroaryl, where each aryl or heteroaryl is optionally substituted with one or more substituents independently selected from $C_{1-6}$ alkyl, $C_{1-6}$ alkoxy, $C_{1-6}$ alkylthio, $C_{1-6}$ alkylsulfonyl, halogen, haloalkyl, cyano, nitro, —C(O)NR$^{a'}$R$^{b'}$, and —NR$^{a'}$R$^{b'}$, where $R^{a'}$ and $R^{b'}$ are each independently selected from the group consisting of hydrogen, $C_{1-9}$ alkyl, and $C_{1-9}$ alkylcarbonyl;

and $R^2$, $R^3$, $R^a$, $R^b$, $R^c$, $R^d$, $R^e$, $R^{a'''}$, and $R^{b'''}$ are as defined hereinabove;

with the proviso that if $R^1$ is —$CR^cR^dR^e$, $R^2$ is hydrogen or alkyl, $R^3$ is a 5- or 6-membered heteroaromatic ring, and
  (i) $R^c$ is hydrogen and one of $R^d$ and $R^e$ is hydrogen or alkyl, then the other of $R^d$ and $R^e$ is other than hydrogen or alkyl if the number of carbon atoms in $R^d$ and $R^e$ together are zero to three; or,
  (ii) $R^c$ is hydrogen and one of $R^d$ and $R^e$ is hydrogen or alkyl, then the other of $R^d$ and $R^e$ is other than alkoxy, alkoxyalkyl, heterocyclyl, heterocyclylalkyl, or heteroalkyl; or,
  (iii) $R^c$ is $NR^{a'''}R^{b'''}$ and one of $R^{a'''}$ and $R^{b'''}$ is hydrogen or $C_{1-3}$ alkyl, then the other of $R^{a'''}$ and $R^{b'''}$ is other than hydrogen or $C_{1-3}$ alkyl.

One embodiment is a compound of formula I wherein $R^1$, $R^2$, $R^3$ are as defined hereinabove.

In another embodiment there is provided a compound of formula II wherein $R^1$, $R^2$, $R^3$ are as defined hereinabove.

In another embodiment there is provided a compound of formula I wherein $R^3$ is a di- or tri-substituted phenyl which substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkyl-aminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl and $R^1$ and $R^2$ are as defined hereinabove.

In another embodiment there is provided a compound of formula I wherein $R^3$ is a 2,4-disubstituted or 2,4,6-trisubstituted phenyl, and the substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl and $R^1$ and $R^2$ are as defined hereinabove.

In another embodiment there is provided a compound of formula I wherein $R^3$ is a 2,4-disubstituted or 2,4,6-trisubstituted phenyl, and the substituents are each independently selected from the group consisting of $C_{1-6}$ alkyl, $C_{1-6}$ alkoxy, $C_{1-6}$ alkylthio, halogen, haloalkyl, cyano, alkylamino, dialkylamino, and nitro, and $R^1$ and $R^2$ are as defined hereinabove.

In another embodiment there is provided a compound of formula I wherein $R^2$ is hydrogen, $C_{1-6}$ alkyl, or $C_{1-6}$ alkylcarbonyl and $R^3$ is a 2,4-disubstituted or 2,4,6-trisubstituted phenyl, and the substituents are each independently selected from the group consisting of $C_{1-6}$ alkyl, $C_{1-6}$ alkoxy, $C_{1-6}$ alkylthio, halogen, haloalkyl, cyano, alkylamino, dialkylamino, and nitro and $R^1$ is as defined hereinabove.

In another embodiment there is provided a compound of formula I wherein $R^1$ is —$CR^cR^dR^e$; $R^c$ is hydroxy; $R^3$ is a di- or tri-substituted phenyl which substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl, and $R^2$, $R^d$ and $R^e$ are as defined herein above.

In another embodiment there is provided a compound of formula I wherein $R^1$ is —$CR^cR^dR^e$; $R^c$ is hydroxy and $R^d$ and $R^e$ are each independently selected from the group consisting of hydrogen, $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally substituted with one or more substituents independently selected from the group consisting of $C_{1-6}$ alkyl, haloalkyl, $C_{1-6}$ alkoxy, and halogen; $R^3$ is a di- or tri-substituted phenyl which substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl, and $R^2$ is as defined hereinabove.

In another embodiment there is provided a compound of formula I wherein $R^1$ is —$CR^cR^dR^e$; $R^c$ is hydroxy and $R^d$ and $R^e$ are each independently selected from the group consisting of $C_{1-9}$ alkyl, $C_{1-6}$ alkoxyalkyl, aryl, and heteroaryl, where each of said aryl or heteroaryl groups is optionally substituted with one or more substituents independently selected from the group consisting of $C_{1-6}$ alkyl, haloalkyl, $C_{1-6}$ alkoxy, and halogen; $R^3$ is a di- or tri-substituted phenyl which substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^2$ is as defined herein above.

In another embodiment there is provided a compound of formula I wherein $R^1$ is —$CR^cR^dR^e$; $R^c$ is hydroxy and $R^d$ and $R^e$ are each independently selected from the group consisting of $C_{1-9}$ alkyl, $C_{1-6}$ alkoxyalkyl, aryl, and heteroaryl, where each of said aryl or heteroaryl groups is optionally substituted with one or more substituents independently selected from the group consisting of $C_{1-6}$ alkyl, haloalkyl, $C_{1-6}$ alkoxy, and halogen; $R^2$ is $C_{1-6}$ alkyl; and $R^3$ is a 2,4-disubstituted or 2,4,6-trisubstituted phenyl, and the substituents are each independently selected from the group consisting of $C_{1-6}$ alkyl, $C_{1-6}$ alkoxy, halogen, haloalkyl, cyano, and —$NR^{a''}R^{b''}$, where $R^{a''}$ and $R^{b''}$ are each independently selected from the group consisting of hydrogen and $C_{1-9}$ alkyl.

In another embodiment there is provided a compound of formula I wherein $R^1$ is —$CR^cR^dR^e$; $R^c$ is hydroxy and $R^d$ and $R^1$ are taken together to form a cycloalkyl or heterocyclyl group; $R^2$ is $C_{1-6}$ alkyl; and $R^3$ is a 2,4-disubstituted or 2,4,6-trisubstituted phenyl, and the substituents are each independently selected from the group consisting of $C_{1-6}$ alkyl, $C_{1-6}$ alkoxy, halogen, haloalkyl, cyano, and —$NR^{a''}R^{b''}$, where $R^{a''}$ and $R^{b''}$ are each independently selected from the group consisting of hydrogen and $C_{1-9}$ alkyl.

In another embodiment there is provided a compound of formula I, wherein $R^1$ is —$CR^cR^dR^e$; $R^e$ is selected from the group consisting of $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally, substituted with one or more substituents independently selected from the group consisting of $C_{1-6}$ alkyl, haloalkyl, $C_{1-6}$ alkoxy, and halogen; $R^c$ and $R^d$ are taken together to form a divalent group selected from $C_{1-6}$ alkylidenyl, $C_{1-6}$ heteroalkylidenyl, $C_{3-6}$ cycloalkylidenyl, $C_{3-6}$ cycloalkyl-alkylidenyl, $C_{3-6}$ cycloalkyl-$C_{1-3}$ alkylalkylidenyl, $C_{3-6}$ heterocyclylidenyl, $C_{3-6}$ heterocyclyl-$C_{1-3}$ alkylidenyl, $C_{3-6}$ heterocyclylalkyl-$C_{1-3}$ alkylidenyl, aryl-$C_{1-3}$ alkylidenyl, aryl-$C_{1-3}$ alkyl-alkylidenyl, heteroaryl-$C_{1-3}$ alkylidenyl, and heteroarylalkyl-$C_{1-3}$ alkylidenyl, wherein each of said cycloalkyl, aryl, or heteroaryl groups is optionally substituted with one or more substituents independently selected from $C_{1-6}$ alkyl, haloalkyl, $C_{1-6}$ alkoxy, amino, alkylamino, dialkylamino, and halogen; $R^3$ is a di- or tri-substituted phenyl which substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl, and $R^1$ is as defined hereinabove.

In another embodiment there is provided a compound of formula I, wherein $R^1$ is —$CR^cR^dR^e$; $R^e$ is selected from the group consisting of $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally substituted with one or more substituents independently selected from the group consisting of $C_{1-6}$ alkyl, haloalkyl, $C_{1-6}$ alkoxy, and halogen; $R^c$ and $R^d$ are taken together to form a divalent group selected from $C_{1-6}$ alkylidenyl, $C_{3-6}$ cycloalkyl-alkylidenyl, aryl-$C_{1-3}$ alkylidenyl, and heteroaryl-$C_{1-3}$ alkylidenyl, wherein each of said aryl or heteroaryl groups is optionally substituted with one or more substituents independently selected from $C_{1-6}$ alkyl, haloalkyl, $C_{1-6}$ alkoxy, amino, alkylamino, dialkylamino, and halogen; $R^3$ is a di- or tri-substituted phenyl which substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl, and $R^2$ is as defined hereinabove.

In another embodiment there is provided a compound of formula I, wherein $R^1$ is —$CR^cR^dR^e$; $R^e$ is selected from the group consisting of $C_{1-9}$ alkyl, $C_{1-6}$ alkoxyalkyl, and heteroaryl, where the heteroaryl is optionally substituted with one or more substituents independently selected from the group consisting of $C_{1-6}$ alkyl, haloalkyl, $C_{1-6}$ alkoxy, and halogen; $R^c$ and $R^d$ are taken together to form a divalent group selected from $C_{1-6}$ alkylidenyl, $C_{3-6}$ cycloalkyl-alkylidenyl, aryl-$C_{1-3}$ alkylidenyl, and heteroaryl-$C_{1-3}$ alkylidenyl, wherein each of said aryl or heteroaryl groups is optionally substituted with one or more substituents independently selected from $C_{1-6}$ alkyl, haloalkyl, $C_{1-6}$ alkoxy, amino, alkylamino, dialkylamino, and halogen; $R^3$ is a di- or tri-substituted phenyl which substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl, and $R^2$ is as defined hereinabove.

In another embodiment there is provided a compound of formula I, wherein $R^1$ is $CR^cR^dR^e$; $R^e$ is hydrogen; and $R^2$, $R^3$, $R^d$ and $R^e$ are as defined hereinabove.

In another embodiment there is provided a compound of formula I wherein $R^1$ is $CR^cR^dR^e$; $R^c$ is hydrogen; $R^d$ and $R^e$ are each independently selected from the group consisting of $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally substituted with one or more substituents independently selected from the group consisting of $C_{1-6}$alkyl, haloalkyl, $C_{1-6}$alkoxy, and halogen and $R^2$, $R^3$ are as defined hereinabove.

In another embodiment there is provided a compound of formula I wherein $R^1$ is $CR^cR^dR^e$; $R^c$ is hydrogen; $R^d$ and $R^e$ are each independently selected from the group consisting of $C_{1-9}$ alkyl, $C_{1-6}$ alkoxyalkyl, aryl, and heteroaryl, where each of said aryl or heteroaryl groups is optionally substituted with one or more substituents independently selected from the group consisting of $C_{1-6}$ alkyl, haloalkyl, $C_{1-6}$ alkoxy, and halogen; $R^2$ is $C_{1-6}$ alkyl; and $R^3$ is a 2,4-disubstituted or 2,4,6-trisubstituted phenyl, and the substituents are independently selected from the group consisting of $C_{1-6}$ alkyl, $C_{1-6}$ alkoxy, halogen, haloalkyl, cyano, and —$NR^{a''}R^{b''}$, where $R^{a''}$ and $R^{b''}$ are each independently selected from the group consisting of hydrogen and $C_{1-9}$ alkyl.

In another embodiment there is provided a compound of formula I wherein $R^1$ is —$NR^aR^b$; —$C(O)NR^aR^b$; or —$CR^c R^dR^e$, where $R^c$ is —$NR^{a'''}R^{b'''}$; $R^d$ and $R^e$ are each independently selected from the group consisting of hydrogen and $C_{1-9}$ alkyl; and $R^2$, $R^3$, $R^a$, $R^b$, $R^{a'''}$, $^{and\ Rb'''}$ are as defined hereinabove.

In another embodiment there is provided a compound of formula I wherein $R^1$ is —$NR^aR^b$; —$C(O)NR^aR^b$; or —$CR^cR^dR^e$, where $R^c$ is —$NR^{a'''}R^{b'''}$; $R^d$ and $R^e$ are each independently selected from the group consisting of hydrogen and $C_{1-9}$ alkyl; $R^a$, $R^b$, $R^{a'''}$ and $R^{b'''}$ are each independently selected from the group consisting of hydrogen, $C_{1-9}$ alkyl, hydroxyalkyl, $C_{1-6}$ alkoxyalkyl, $C_{3-6}$ cycloalkyl-$C_{1-3}$ alkyl, heterocyclylalkyl, arylalkyl, and heteroarylalkyl, wherein each of said aryl or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; and, $R^2$ and $R^3$ are as defined hereinabove.

In another embodiment there is provided a compound of formula I wherein $R^1$ is —$NR^aR^b$; —$C(O)NR^aR^b$; or —$CR^c R^dR^e$, where $R^c$ is —$NR^{a'''}R^{b'''}$; $R^d$ and $R^e$ are each independently selected from the group consisting of hydrogen and $C_{1-9}$ alkyl; $R^a$ and $R^b$, or, $R^{a'''}$ and $R^{b'''}$ are taken together with the nitrogen to which they are attached form an heterocyclyl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, and imidazoline, where each of said rings is optionally substituted with one or more substituents independently selected from the group consisting of hydroxy, oxo, alkyl, aminoalkyl, acyl, acylamino, aminocarbonyl, aminocarbonylalkyl, and aminocarbonylamino, and each of said amino groups is optionally monosubstituted or disubstituted with alkyl, or is contained in a pyrrolidinyl, piperidinyl, morpholinyl, or piperazinyl group; and, $R^2$ and $R^3$ are as defined hereinabove.

In another embodiment there is provided a compound of formula I wherein $R^1$ is —$NR^aR^b$; $R^a$ is selected from the group consisting of hydrogen, $C_{1-9}$ alkyl, and $C_{1-6}$ alkoxyalkyl; and $R^b$ is selected from the group consisting of $C_{1-9}$ alkyl, hydroxyalkyl,$C_{3-6}$ cycloalkyl-$C_{1-3}$ alkyl, $C_{1-6}$ alkoxyalkyl, heterocyclylalkyl, arylalkyl, and heteroarylalkyl, wherein each of said aryl or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; $R^3$ is a di- or tri-substituted phenyl which substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and $R^2$ is as defined hereinabove.

In another embodiment there is provided a compound of formula I wherein $R^1$ is $-NR^aR^b$; $R^a$ is selected from the group consisting of hydrogen, $C_{1-9}$ alkyl, and $C_{1-6}$alkoxyalkyl; and $R^b$ is selected from the group consisting of $C_{1-9}$ alkyl, $C_{3-6}$ cycloalkyl-Cl$_3$ alkyl, hydroxyalkyl, $C_{1-6}$ alkoxyalkyl, heterocyclylalkyl, arylalkyl, and heteroarylalkyl, wherein each of said aryl or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; $R^2$ is $C_{1-6}$ alkyl; and $R^3$ is a 2,4-disubstituted or 2,4,6-trisubstituted phenyl, and the substituents are independently selected from the group consisting of $C_{1-6}$ alkyl, $C_{1-6}$ alkoxy, halogen, haloalkyl, cyano, and $-NR^{a''}R^{b''}$, where $R^{a''}$ and $R^{b''}$ are each independently selected from the group consisting of hydrogen and $C_{1-9}$ alkyl.

In another embodiment there is provided a compound of formula I wherein $R^1$ is $-CR^cR^dR^e$; $R^c$ is $-NR^{a'''}R^{b'''}$; $R^d$ and $R^e$ are each independently selected from the group consisting of hydrogen and $C_{1-9}$alkyl; $R^{a'''}$ is selected from the group consisting of hydrogen, $C_{1-9}$ alkyl, and $C_{1-6}$ alkoxyalkyl; $R^{b'''}$ is selected from the group consisting of $C_{1-9}$ alkyl, $C_{3-6}$ cycloalkyl-$C_{1-3}$ alkyl, hydroxyalkyl, $C_{1-6}$ alkoxyalkyl, heterocyclylalkyl, arylalkyl, and heteroarylalkyl, wherein each of said aryl or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; $R^3$ is a di- or tri-substituted phenyl which substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and $R^2$ is as defined hereinabove.

In another embodiment there is provided a compound of formula I wherein $R^1$ is $-CR^cR^dR^e$; $R^c$ is $-NR^{a'''}R^{b'''}$; $R^d$ and $R^e$ are each independently selected from the group consisting of hydrogen and $C_{1-9}$ alkyl; $R^{a'''}$ is selected from the group consisting of hydrogen, $C_{1-9}$ alkyl, and $C_{1-6}$ alkoxyalkyl; $R^{b'''}$ is selected from the group consisting of $C_{1-9}$ alkyl, $C_{3-6}$ cycloalkyl-$C_{1-3}$ alkyl,hydroxyalkyl, $C_{1-6}$ alkoxyalkyl, heterocyclylalkyl, arylalkyl, and heteroarylalkyl, wherein each of said aryl or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; $R^2$ is $C_{1-6}$ alkyl; and $R^3$ is a 2,4-disubstituted or 2,4,6-trisubstituted phenyl, and the substituents are independently selected from the group consisting of $C_{1-6}$ alkyl, $C_{1-6}$ alkoxy, halogen, haloalkyl, cyano, and $-NR^{a''}R^{b''}$, where $R^{a''}$ and $R^{b''}$ are each independently selected from the group consisting of hydrogen and $C_{1-9}$ alkyl.

In another embodiment there is provided a compound of formula I wherein $R^1$ is aryl or heteroaryl, where said aryl or heteroaryl is optionally substituted with one or more substituents independently selected from $C_{1-6}$ alkyl, $C_{1-6}$ alkoxy, $C_{1-6}$ alkylthio, $C_{1-6}$ alkylsulfonyl, halogen, haloalkyl, cyano, nitro, and $-NR^{a'}R^{b'}$, where $R^{a'}$ and $R^{b'}$ are each independently selected from the group consisting of hydrogen, $C_{1-9}$ alkyl, and $C_{1-9}$ alkylcarbonyl; $R^3$ is a di- or tri-substituted phenyl which substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and $R^2$ is as defined hereinabove.

In another embodiment there is provided a compound of formula I wherein $R^1$ is aryl or heteroaryl and said aryl or heteroaryl is optionally substituted with one or more substituents independently selected from $C_{1-6}$ alkyl, $C_{1-6}$ alkoxy, halogen, haloalkyl, cyano, and $-NR^{a'Rb'}$, where $R^{a'}$ and $R^{b'}$ are each independently selected from the group consisting of hydrogen, $C_{1-9}$ alkyl, and $C_{1-9}$ alkylcarbonyl $R^3$ is a di- or tri-substituted phenyl which substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and $R^2$ is as defined hereinabove.

In another embodiment there is provided a compound of formula I wherein $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^1$ and $R^2$ are as defined hereinabove.

In another embodiment there is provided a compound of formula I wherein $R^3$ is a 2,4-disubstituted, 2,6-disubstituted, or 2,4,6-trisubstituted pyridin-3-yl, said the substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^1$ and $R^2$ are as defined hereinabove.

In another embodiment there is provided a compound of formula I wherein $R^3$ is a 2,4-disubstituted, 2,6-disubstituted, or 2,4,6-trisubstituted pyridin-3-yl, and said substituents are each independently selected from the group consisting of $C_{1-6}$ alkyl, $C_{1-6}$ alkoxy, halogen, haloalkyl, alkylamino, and dialkylamino; and, $R^1$ and $R^2$ are as defined hereinabove.

In another embodiment there is provided a compound of formula I wherein $R^3$ is a 2,4-disubstituted, 2,6-disubstituted, or 2,4,6-trisubstituted pyridin-3-yl, and said substituents are each independently selected from the group consisting of $C_{1-6}$ alkyl, $C_{1-6}$ alkoxy, halogen, haloalkyl, alkylamino, and dialkylamino; $R^2$ is hydrogen, $C_{1-6}$ alkyl, or $C_{1-6}$ alkylcarbonyl; and $R^1$ is as defined hereinabove.

In another embodiment there is provided a compound of formula I wherein $R^1$ is —$CR^cR^dR^e$; $R^c$ is hydroxy; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^2$, $R^d$ and $R^e$ are as defined hereinabove.

In another embodiment there is provided a compound of formula I wherein $R^1$ is —$CR^cR^dR^e$; $R^c$ is hydroxy; $R^d$ and $R^e$ are each independently selected from the group consisting of hydrogen, $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally substituted with one or more substituents independently selected from the group consisting of $C_{1-6}$ alkyl, haloalkyl, $C_{1-6}$ alkoxy, and halogen; $R^3$ is a di- or tri-substituted pyridinyl, and said substituents are each independently selected from the group consisting of $C_{1-6}$ alkyl, $C_{1-6}$ alkoxy, $C_{1-6}$ alkylthio; $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^2$ is as defined hereinabove.

In another embodiment there is provided a compound of formula I wherein $R^1$ is —$CR^cR^dR^e$; $R^c$ is hydroxy; $R^d$ and $R^e$ are each independently selected from the group consisting of $C_{1-9}$ alkyl, $C_{1-6}$ alkoxyalkyl, aryl, and heteroaryl, where each of said aryl or heteroaryl groups is optionally substituted with one or more substituents independently selected from the group consisting of $C_{1-6}$ alkyl, haloalkyl, $C_{1-6}$ alkoxy, and halogen; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and $R^3$ is as defined hereinabove.

In another embodiment there is provided a compound of formula I wherein $R^1$ is —$CR^cR^dR^e$; $R^c$ is hydroxy; $R^d$ and $R^e$ are each independently selected from the group consisting of $C_{1-9}$ alkyl, $C_{1-6}$ alkoxyalkyl, aryl, and heteroaryl, where each of said aryl or heteroaryl groups is optionally substituted with one or more substituents independently selected from the group consisting of $C_{1-6}$ alkyl, haloalkyl, $C_{1-6}$ alkoxy, and halogen; $R^2$ is $C_{1-6}$ alkyl; and $R^3$ is a 2,4-disubstituted, 2,6-disubstituted or 2,4,6-trisubstituted pyridin-3-yl, and the substituents are each independently selected from the group consisting of $C_{1-6}$ alkyl, $C_{1-6}$ alkoxy, halogen, haloalkyl, and —$NR^{a''}R^{b''}$, where $R^{a''}$ and $R^{b''}$ are each independently selected from the group consisting of hydrogen and $C_{1-9}$ alkyl.

In another embodiment there is provided a compound of formula I wherein $R^1$ is —$CR^cR^dR^e$; $R^c$ is hydroxy; wherein $R^d$ and $R^e$ are taken together to form a cycloalkyl or heterocyclyl group; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^2$ is as defined hereinabove.

In another embodiment there is provided a compound of formula I wherein $R^1$ is —$CR^cR^dR^e$; $R^e$ is selected from the group consisting of $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally substituted with one or more substituents independently selected from the group consisting of $C_{1-6}$ alkyl, haloalkyl, $C_1$alkoxy, and halogen; $R^c$ and $R^d$ are taken together to form a divalent group selected from $C_{1-6}$ alkylidenyl, $C_{1-6}$ heteroalkylidenyl, $C_{3-6}$ cycloalkylidenyl, $C_{3-6}$ cycloalkyl-alkylidenyl, $C_{3-6}$ cycloalkyl-$C_{1-3}$ alkylalkylidenyl, $C_{3-6}$ heterocyclylidenyl, $C_{3-6}$ heterocyclyl-$C_{1-3}$ alkylidenyl, $C_{3-6}$ heterocyclylalkyl-$C_{1-3}$ alkylidenyl, aryl-$C_{1-3}$ alkylidenyl, aryl-$C_{1-3}$ alkyl-alkylidenyl, heteroaryl-$C_{1-3}$ alkylidenyl, and heteroarylalkyl-$C_{1-3}$ alkylidenyl, wherein each of said cycloalkyl, aryl, or heteroaryl groups is optionally substituted with one or more substituents independently selected from $C_{1-6}$ alkyl, haloalkyl, $C_{1-6}$ alkoxy, amino, alkylamino, dialkylamino, and halogen; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^2$ is as defined hereinabove.

In another embodiment there is provided a compound of formula I wherein $R^1$ is —$CR^cR^dR^e$; $R^e$ is selected from the group consisting of $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally substituted with one or more substituents independently selected from the group consisting of $C_{1-6}$ alkyl, haloalkyl, $C_{1-6}$ alkoxy, and halogen; $R^c$ and $R^d$ are taken together to form a divalent group selected from $C_{1-6}$ alkylidenyl, $C_{3-6}$ cycloalkyl-alkylidenyl, $C_{3-6}$ heterocyclylidenyl, aryl-$C_{1-3}$ alkylidenyl, and heteroaryl-$C_{1-3}$ alkylidenyl, wherein each of said cycloalkyl, aryl, or heteroaryl groups is optionally substituted with one or more substituents independently selected from $C_{1-6}$ alkyl, haloalkyl, $C_{1-6}$ alkoxy, amino, alkylamino, dialkylamino, and halogen; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, and $R^2$ are as defined hereinabove.

In another embodiment there is provided a compound of formula I wherein $R^1$ is —$CR^cR^dR^e$; $R^e$ is selected from the group consisting of $C_{1-9}$ alkyl, $C_{1-6}$ alkoxyalkyl, and heteroaryl, where the heteroaryl is optionally substituted with one or more substituents independently selected from the group consisting of $C_{1-6}$ alkyl, haloalkyl, $C_{1-6}$ alkoxy, and halogen; and $R^c$ and $R^d$ are taken together to form a divalent group selected from $C_{1-6}$ alkylidenyl, $C_{3-6}$ cycloalkyl-alkylidenyl, $C_{3-6}$ heterocyclyl-$C_{1-3}$ alkylidenyl, aryl-$C_{1-3}$ alkylidenyl, and heteroaryl-$C_{1-3}$ alkylidenyl, wherein each of said aryl, or heteroaryl groups is optionally substituted with one or more substituents independently selected from $C_{1-6}$ alkyl, $C_{1-6}$ alkoxy, amino, alkylamino, and dialkylamino; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, and $R^2$ are as defined hereinabove.

In another embodiment there is provided a compound of formula I, wherein $R^1$ is —$CR^cR^dR^e$; $R^c$ is hydrogen; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^2$, $R^d$ and $R^e$ are as defined hereinabove.

In another embodiment there is provided a compound of formula I, wherein $R^1$ is —$CR^cR^dR^e$; $R^c$ is hydrogen; $R^d$ and $R^e$ are each independently selected from the group consisting of $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally substituted with one or more substituents independently selected from the group consisting of $C_{1-6}$ alkyl, haloalkyl, $C_{1-6}$ alkoxy, and halogen; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^2$ is as defined hereinabove.

In another embodiment there is provided a compound of formula I wherein $R^1$ is —$CR^cR^dR^e$; $R^c$ is hydrogen; $R^d$ and $R^e$ are each independently selected from the group consisting of $C_{1-9}$ alkyl, $C_{1-6}$ alkoxyalkyl, aryl, and heteroaryl, where each of said aryl or heteroaryl groups is optionally substituted with one or more substituents independently selected from the group consisting of $C_{1-6}$ alkyl, haloalkyl, $C_{1-6}$ alkoxy, and halogen; $R^2$ is $C_{1-6}$ alkyl; and $R^3$ is a 2,4-disubstituted, 2,6-disubstituted, or 2,4,6-trisubstituted pyridin-3-yl, and the substituents are independently selected from the group consisting of $C_{1-6}$ alkyl, $C_1$alkoxy, halogen, haloalkyl, and —$NR^{a''}R^{b''}$, where $R^{a''}$ and $R^{b''}$ are each independently selected from the group consisting of hydrogen and $C_{1-9}$ alkyl.

In another embodiment there is provided a compound of formula I wherein $R^1$ is —$NR^aR^b$; —$C(O)NR^aR^b$; or —$CR^c R^dR^e$, where $R^c$ is —$NR^{a'''}R^{b'''}$; $R^d$ and $R^e$ are each independently selected from the group consisting of hydrogen and $C_{1-9}$ alkyl; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^2$, $R^a$, $R^b$, $R^{a'''}$, and $R^{b'''}$ are as defined hereinabove.

In another embodiment there is provided a compound of formula I wherein $R^1$ is —$NR^aR^b$; —$C(O)NR^aR^b$; or —$CR^c R^dR^e$, where $R^c$ is —$NR^{a'''}R^{b'''}$; $R^d$ and $R^e$ are each independently selected from the group consisting of hydrogen and $C_{1-9}$ alkyl; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; $R^a$, $R^b$, $R^{a'''}$, and $R^{b'''}$ are each independently selected from the group consisting of hydrogen, $C_{1-9}$ alkyl, hydroxyalkyl, $C_{1-6}$ alkoxyalkyl, $C_{3-6}$ cycloalkyl-$C_{1-3}$ alkyl, heterocyclylalkyl, arylalkyl, and heteroarylalkyl, wherein each of said aryl or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; and, $R^2$ is as defined hereinabove.

In another embodiment there is provided a compound of formula I wherein $R^1$ is —$NR^aR^b$; —$C(O)NR^aR^b$; or —$CR^c R^dR^e$, where $R^c$ is —$NR^{a'''}R^{b'''}$; $R^d$ and $R^e$ are each independently selected from the group consisting of hydrogen and $C_{1-9}$ alkyl; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; $R^a$ and $R^b$, or $R^{a'''}$ and $R^{b'''}$, are taken together with the nitrogen to which they are attached form an heterocyclyl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, and imidazoline, where each of said rings is optionally substituted with one or more substituents independently selected from the group consisting of hydroxy, oxo, alkyl, aminoalkyl, acyl, acylamino, aminocarbonyl, aminocarbonylalkyl, and aminocarbonylamino, and each of said amino groups is optionally monosubstituted or disubstituted with alkyl, or is contained in a pyrrolidinyl, piperidinyl, morpholinyl, or piperazinyl group; and, $R^2$ is as defined hereinabove.

In another embodiment there is provided a compound of formula I wherein $R^1$ is —$NR^aR^b$; $R^a$ is selected from the group consisting of hydrogen, $C_{1-9}$ alkyl, and $C_{1-6}$ alkoxyalkyl; $R^b$ is selected from the group consisting of $C_{1-9}$ alkyl, $C_{3-6}$ cycloalkyl-$C_{1-3}$ alkyl, hydroxyalkyl, $C_{1-6}$ alkoxyalkyl, heterocyclylalkyl, arylalkyl, and heteroarylalkyl, wherein each of said aryl or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^2$ is as defined hereinabove.

In another embodiment there is provided a compound of formula I wherein $R^1$ is —$NR^aR^b$; $R^a$ is selected from the group consisting of hydrogen, $C_{1-9}$ alkyl, and $C_{1-6}$ alkoxyalkyl; $R^b$ is selected from the group consisting of $C_{1-9}$ alkyl, $C_{3-6}$ cycloalkyl-$C_{1-3}$ alkyl, hydroxyalkyl, $C_{1-6}$ alkoxyalkyl, heterocyclylalkyl, arylalkyl, and heteroarylalkyl, wherein each of said aryl or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; $R^2$ is $C_{1-6}$ alkyl; and $R^3$ is a 2,4-disubstituted, 2,6-disubstituted, or 2,4,6-trisubstituted pyridin-3-yl, and the substituents are independently selected from the group consisting of $C_{1-6}$ alkyl, $C_{1-6}$ alkoxy, halogen, haloalkyl, and —$NR^{a''}R^{b''}$, where $R^{a''}$ and $R^{b''}$ are each independently selected from the group consisting of hydrogen and $C_{1-9}$ alkyl.

In another embodiment there is provided a compound of formula I wherein $R^1$ is —$CR^cR^dR^e$; $R^c$ is $NR^{a''}R^{b''}$; $R^d$ and $R^e$ are each independently selected from the group consisting of hydrogen and $C_{1-9}$ alkyl; $R^{a''}$ is selected from the group consisting of hydrogen, $C_{1-9}$ alkyl, and $C_{1-6}$ alkoxyalkyl; $R^{b'''}$ is selected from the group consisting of $C_{1-9}$ alkyl, $C_{3-6}$ cycloalkyl-$C_{1-3}$ alkyl, hydroxyalkyl, $C_{1-6}$ alkoxyalkyl, heterocyclylalkyl, arylalkyl, and heteroarylalkyl, wherein each of said aryl or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, and $R^2$ are as defined hereinabove.

In another embodiment there is provided a compound of formula I wherein $R^1$ is —$CR^cR^dR^e$; $R^c$ is $NR^{a''}R^{b''}$; $R^d$ and $R^e$ are each independently selected from the group consisting of hydrogen and $C_{1-9}$ alkyl; $R^{a'''}$ is selected from the group consisting of hydrogen, $C_{1-9}$ alkyl, and $C_{1-6}$ alkoxyalkyl; $R^{b'''}$ is selected from the group consisting of $C_{1-9}$ alkyl, $C_{3-6}$ cycloalkyl-$C_{1-3}$ alkyl, hydroxyalkyl, $C_{1-6}$ alkoxyalkyl, heterocyclylalkyl, arylalkyl, and heteroarylalkyl, wherein each of said aryl or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; $R^2$ is $C_{1-6}$ alkyl; and $R^3$ is a 2,4-disubstituted, 2,6-disubstituted, or 2,4,6-trisubstituted pyridin-3-yl, and the substituents are independently selected from the group consisting of $C_{1-6}$ alkyl, $C_{1-6}$ alkoxy, halogen, haloalkyl, and —$NR^{a''}R^{b''}$, where $R^{a''}$ and $R^{b''}$ are each independently selected from the group consisting of hydrogen and $C_{1-9}$ alkyl.

In another embodiment there is provided a compound of formula I wherein $R^1$ is aryl or heteroaryl, where said aryl or heteroaryl is optionally substituted with one or more substituents independently selected from $C_{1-6}$ alkyl, $C_{1-6}$ alkoxy, $C_{1-6}$ alkylthio, $C_{1-6}$ alkylsulfonyl, halogen, haloalkyl, cyano, nitro, and —$NR^{a'}R^{b'}$, where $R^{a'}$ and $R^{b'}$ are each independently selected from the group consisting of hydrogen, $C_{1-9}$ alkyl, and $C_{1-9}$ alkylcarbonyl; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^2$ is as defined hereinabove.

In another embodiment there is provided a compound of formula I wherein $R^1$ is aryl or heteroaryl, where said aryl or heteroaryl is optionally substituted with one or more substituents independently selected from $C_{1-6}$ alkyl, $C_{1-6}$ alkoxy, halogen, haloalkyl, cyano, and —$NR^{a'}R^{b'}$, where $R^{a'}$ and $R^{b'}$ are each independently selected from the group consisting of hydrogen, $C_{1-9}$ alkyl, and $C_{1-9}$ alkylcarbonyl; $R^3$ is a di- or tri-substituted pyridinyl, and said substituents are each independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl; and, $R^2$ is as defined hereinabove.

In another embodiment there is provided a pharmaceutical composition comprising a therapeutically effective amount of at least one compound of formula I in admixture with at least one pharmaceutically acceptable carrier.

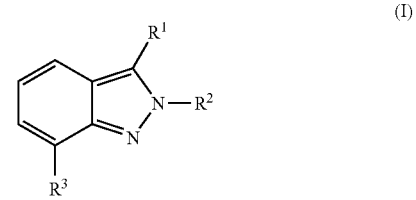

(I)

wherein $R^1$, $R^2$, $R^3$, $R^a$, $R^b$, $R^c$, $R^d$, $R^e$, $R^{a'''}$ and $R^{b'''}$ are as defined hereinabove; or, individual isomers, racemic or non-racemic mixtures of isomers, or pharmaceutically acceptable salts thereof; or, In another embodiment there is provided a method for treating a subject having a disease state that is alleviated by treatment with a CRF receptor antagonist, which comprises administering to such a subject a therapeutically effective amount of a compound of formula I

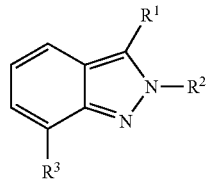
(I)

wherein $R^1$, $R^2$, $R^3$, $R^a$, $R^b$, $R^c$, $R^d$, $R^e$, $R^{a'''}$ and $R^{b'''}$ are as defined hereinabove; or, individual isomers, racemic or non-racemic mixtures of isomers, or pharmaceutically acceptable salts thereof; or, In another embodiment there is provided a method for treating a subject having a disease state that is alleviated by treatment with a CRF receptor antagonist wherein the disease state is selected from the group consisting of phobias, stress-related illnesses, mood disorders, eating disorders, generalized anxiety disorders, stress-induced gastrointestinal dysfunctions, neurodegenerative diseases, and neuropsychiatric disorders, which comprises administering to such a subject a therapeutically effective amount of a compound of formula I,

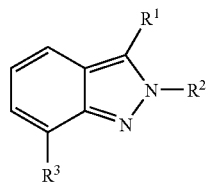
(I)

wherein $R^1$, $R^2$, $R^3$, $R^a$, $R^b$, $R^c$, $R^d$, $R^e$, $R^{a'''}$ and $R^{b'''}$ are as defined hereinabove; or, individual isomers, racemic or non-racemic mixtures of isomers, or pharmaceutically acceptable salts thereof.

In another embodiment there is provided a compound of Formula II

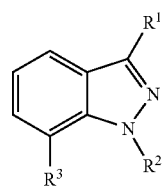
(II)

wherein:
$R^1$ is —$NR^aR^b$, —$CR^cR^dR^e$, $CO_2R^a$; or, $R^1$ is hydrogen, cycloalkenyl, aryl, or heteroaryl, where each aryl or heteroaryl is optionally substituted with one or more substituents independently selected from $C_{1-6}$ alkyl, $C_{1-6}$ alkoxy, $C_{1-6}$ alkylthio, $C_{1-6}$ alkylsulfonyl, halogen, haloalkyl, cyano, nitro, —$C(O)NR^{a'}R^{b'}$, and —$NR^{a'}R^{b'}$, where $R^{a'}$ and $R^{b'}$ are each independently selected from the group consisting of hydrogen, $C_{1-9}$ alkyl, and $C_{1-9}$ alkylcarbonyl;

$R^2$ is hydrogen, $C_{1-6}$ alkyl, $C_{3-6}$ cycloalkyl, $C_{3-6}$ cycloalkyl-$C_{1-3}$ alkyl, $C_{1-6}$ alkylcarbonyl, $C_{1-6}$ alkylsulfonyl, aryl, or arylalkyl, wherein said aryl or arylalkyl is optionally substituted with one or more substituents independently selected from $C_{1-6}$ alkyl, haloalkyl, $C_{1-6}$ alkoxy, and halogen;

$R^3$ is aryl or heteroaryl, each optionally substituted with one or more substituents independently Oselected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —$NR^{a''}R^{b''}$, where $R^{a''}$ and $R^{b''}$ are each independently selected from the group consisting of hydrogen, $C_{1-9}$ alkyl, and $C_{1-9}$ alkylcarbonyl;

$R^a$ and $R^b$ are each independently selected from the group consisting of hydrogen, $C_{1-9}$ alkyl, hydroxyalkyl, $C_{1-6}$ alkoxyalkyl, $C_{1-6}$ alkylthioalkyl, carboxyalkyl, acyl, $C_{3-6}$ cycloalkyl, $C_{3-6}$ cycloalkyl-$C_{1-3}$ alkyl, di-$C_{3-6}$ cycloalkyl$C_{1-3}$ alkyl, $C_{1-6}$ heteroalkyl, aminoalkyl, aminocarbonylalkyl, cyanoalkyl, $C_{5-8}$ heterocyclyl, heterocyclylalkyl, aryl, arylalkyl, heteroaryl, heteroarylalkyl, phenylalkyl, diphenylalkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or $R^a$ and $R^b$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$ alkyl, haloalkyl, $C_{1-6}$ alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group;

$R^c$ is hydrogen, hydroxy, $C_{1-6}$alkoxy, or —$NR^{a'''}R^{b'''}$;

$R^d$ and $R^e$ are each independently selected from the group consisting of hydrogen, $C_{1-9}$ alkyl, hydroxyalkyl, $C_{1-6}$ alkoxyalkyl, $C_{1-6}$ alkylthioalkyl, heteroalkyl, heterocyclyl, heterocyclylalkyl, $C_{3-6}$ cycloalkyl, $C_{3-6}$ cycloalkyl-$C_{1-3}$ alkyl, di-$C_{3-6}$ cycloalkyl-$C_{1-3}$ alkyl, aryl, arylalkyl, heteroaryl, heteroarylalkyl, phenylalkyl, diphenyl-$C_{1-3}$ alkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, and halogen; or $R^c$ and $R^d$ are taken together to form a divalent group selected from $C_{1-6}$ alkylidenyl, $C_{1-6}$ heteroalkylidenyl, $C_{3-6}$ cycloalkylidenyl, $C_{3-6}$ cycloalkyl-alkylidenyl, $C_{3-6}$ cycloalkylalkyl-$C_{1-3}$ alkylidenyl, $C_{3-6}$ heterocyclylidenyl, $C_{3-6}$ heterocyclyl-$C_{1-3}$ alkylidenyl, $C_{3-6}$ heterocyclylalkyl-$C_{1-3}$ alkylidenyl, aryl-$C_{1-3}$ alkylidenyl, aryl-$C_{1-3}$ alkyl-alkylidenyl, heteroaryl-$C_{1-3}$ alkylidenyl, and heteroarylalkyl-$C_{1-3}$ alkylidenyl, wherein each of said cycloalkyl, aryl, or heteroaryl groups is optionally substituted with one or more substituents independently selected from $C_{1-6}$ alkyl, haloalkyl, $C_{1-6}$ alkoxy, amino, alkylamino, dialkylamino, and halogen; or $R^d$ and $R^e$ are taken together with the carbon to which they are attached to form a cycloalkyl or heterocyclyl ring;

$R^{a'''}$ and $R^{b'''}$ are each independently selected from the group consisting of hydrogen, $C_{1-9}$ alkyl, hydroxyalkyl, $C_{1-6}$ alkoxyalkyl, $C_{1-6}$ alkylthioalkyl, carboxyalkyl, acyl, $C_{3-6}$ cycloalkyl, $C_{3-6}$ cycloalkyl-$C_{1-3}$ alkyl, di-$C_{3-6}$ cycloalkyl-$C_{1-3}$ alkyl, $C_{1-6}$ heteroalkyl, aminoalkyl, aminocarbonylalkyl, cyanoalkyl, $C_{5-8}$ heterocyclyl, heterocyclylalkyl, aryl, arylalkyl, heteroaryl, heteroarylalkyl, phenylalkyl, diphenyl-$C_{1-3}$ alkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or $R^{a'''}$ and $R^{b'''}$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$ alkyl, haloalkyl, $C_{1-6}$ alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group; or, individual isomers, racemic or non-racemic mixtures of isomers, or pharmaceutically acceptable salts thereof;

with the proviso that if $R^1$ is —$CR^cR^dR^e$, $R^2$ is hydrogen or alkyl, $R^3$ is a 5- or 6-membered heteroaryl ring, and
  (i) $R^c$ is hydrogen and one of $R^d$ and $R^e$ is hydrogen or alkyl, then the other of $R^d$ and $R^e$ is other than hydrogen or alkyl if the number of carbon atoms in $R^d$ and $R^e$ together are zero to three; or,
  (ii) $R^c$ is hydrogen and one of $R^d$ and $R^e$ is hydrogen or alkyl, then the other of $R^d$ and $R^e$ is other than alkoxy, alkoxyalkyl, heterocyclyl, heterocyclylalkyl, or heteroalkyl; or,
  (iii) $R^c$ is $NR^{a'''}R^{b'''}$ and one of $R^{a'''}$ and $R^{b'''}$ is hydrogen or $C_{1-3}$ alkyl, then the other of $R^{a'''}$ and $R^{b'''}$ is other than hydrogen or $C_{1-3}$ alkyl.

Definitions

Unless otherwise stated, the following terms used in this Application, including the specification and claims, have the definitions given below.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition provided in the Detailed Description of the Invention.

The term "alkyl" as used herein means a monovalent unbranched or branched saturated hydrocarbon radical, consisting solely of carbon and hydrogen atoms, having from one to ten carbon atoms inclusive, unless otherwise indicated. Examples of alkyl radicals include, but are not limited to, methyl, ethyl, propyl, iso-propyl, iso-butyl, sec-butyl, tert-butyl, pentyl, n-hexyl, and the like. The term "lower alkyl" lower alkyl refers to alkyl group having from one to six carbon atoms.

The term "alkylene" as used herein means a divalent unbranched or branched saturated hydrocarbon radical consisting solely of carbon and hydrogen atoms, having from one to ten carbon atoms inclusive, unless otherwise indicated. Examples of alkylene radicals include, but are not limited to, methylene, ethylene, propylene, 2-methylethylene, 3-methylpropylene, 2-ethylethylene, pentylene, hexylene, and the like.

The term "alkoxy" as used herein means a radical —OR, wherein R is a lower alkyl radical as defined herein. Examples of alkoxy radicals include, but are not limited to, methoxy, ethoxy, isopropoxy, and the like.

The term "alkoxyalkyl" as used herein refers to the radical R'R"—, wherein R' is an alkoxy radical as defined herein, and R" is an alkylene radical as defined herein with the understanding that the attachment point of the alkoxyalkyl moiety will be on the alkylene radical. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, propyloxypentyl including their isomers.

The term "cycloalkyl" as used herein means a monovalent saturated carbocyclic radical consisting of one or more rings, and consisting solely of carbon and hydrogen atoms, having from three to eight carbon atoms inclusive, unless otherwise indicated. Examples of cycloalkyl radicals include, but are not limited to, cyclopropyl, cyclobutyl, cyclopentyl, cycloheptyl, and the like.

The term "substituted cycloalkyl" as used herein means the cycloalkyl as defined herein, including one to three substituents, such as hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, and sulfonylamino. Examples of cycloalkyl radicals include, but are not limited to, 3-ethylcyclobutyl, 4-hydroxycyclohexyl 3-chlorcyclopentyl and the like.

The term "cycloalkylalkyl" as used herein means a radical —R'R", wherein R' is an alkylene radical, and R" is a cycloalkyl or substituted cycloalkyl radical as defined herein. Examples of cycloalkylalkyl radicals include, but are not limited to, cyclopropylmethyl, cyclohexylmethyl, cyclopentylethyl, and the like.

The term "cycloalkenyl" as used herein means a monovalent unsaturated carbocyclic radical consisting of one or more rings, and consisting solely of carbon and hydrogen atoms, having from one to ten carbon atoms inclusive, unless otherwise indicated. Examples of cycloalkenyl radicals include, but are not limited to, cyclobuten-1-yl, cyclopenten-1-yl and the like.

The term "substituted cycloalkenylyl" as used herein means the cycloalkenyl as defined herein, including one to three substituents, such as hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, and sulfonylamino, unless otherwise indicated. Examples of substituted cycloalkenyl radicals include, but are not limited to 3-ethylcyclobuten-1-yl, 3-fluorocyclohepten-1-yl, and the like.

The term "halogen" or "halo" as used herein means the radical fluoro, bromo, chloro, or iodo, and combinations thereof.

The term "haloalkyl" as used herein means a lower alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

The term "aryl" or "aromatic" as used herein means a monocyclic or bicyclic radical of 6 to 12 ring carbon atoms having at least one aromatic ring, with the understanding that the attachment point of the aryl radical will be on an aromatic ring. The aryl radical is optionally substituted independently with one or more substituents selected from alkyl, haloalkyl, hydroxyalkyl, heteroalkyl, acyl, acylamino, amino, alkylamino, dialkylamino, alkylthio, alkylsulfinyl, alkylsulfonyl, alkylsulfonyloxy, —$SO_2NR'R''$ (where R' and R" are independently hydrogen or alkyl), alkoxy, haloalkoxy, alkoxycarbonyl, carbamoyl, hydroxy, halo, nitro, cyano, thio, methylenedioxy or ethylenedioxy. More specifically the term aryl includes, but is not limited to, phenyl, naphthyl, tetrahydronaphthyl, 3,4-methylenedioxyphenyl, 1,2,3,4-tetrahydroquinolin-7-yl, 1,2,3,4-tetrahydro-isoquinoline-7-yl, and the like.

The terms "heteroaryl" and "heteroaromatic" as used herein means a monocyclic or bicyclic radical of 5 to 12 ring atoms having at least one aromatic ring containing one, two, or three ring heteroatoms selected from nitrogen, oxygen, and sulfur, the remaining ring atoms being carbon, with the understanding that the attachment point of the heteroaryl radical will be on an aromatic ring. The heteroaryl ring is optionally substituted independently with one or more substituents selected from alkyl, haloalkyl, hydroxyalkyl, heteroalkyl, acyl, acylamino, amino, alkylamino, dialkylamino, alkylthio, alkylsulfinyl, alkylsulfonyl, alkylsulfonyloxy, —$SO_2NR'R''$ (where R' and R" are independently hydrogen or alkyl), alkoxy, haloalkoxy, alkoxycarbonyl, carbamoyl, hydroxy, halo, nitro, cyano, thio, methylenedioxy or ethylenedioxy. Examples of heteroaryl moieties include monocyclic aromatic heterocycles having 5 to 6 ring atoms and 1 to 2 heteroatoms include, but is not limited to, including, and includes, but is not limited to, pyridinyl, furanyl, thienyl, thiazolyl, isothiazolyl, triazolyl, imidazolyl, isoxazolyl, pyrrolyl, pyrazolyl, and pyrimidinyl, and derivatives thereof; and bicyclic aromatic moieties having 9 to 10 ring atoms, including 1 to 3 heteroatoms, and includes, but is not limited to, benzofuranyl, tetrahydrobenzofuranyl, isobenzofuranyl, benzothiazolyl, benzoisothiazolyl, benzotriazolyl, indolyl, isoindolyl, benzoxazolyl, quinolinyl, 5,6,7,8-tetrahydroquinolinyl, isoquinolinyl, 5,6,7,8-tetrahydroisoquinolinyl, benzimidazolyl, benzisoxazolyl, and benzothienyl, and derivatives thereof.

The term "heteroalkyl" as used herein means an alkyl radical as defined herein wherein one, two, or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkyl-$C_{1-3}$ alkyl; and $R^b$ and $R^c$ are independently selected from the group consisting of hydrogen, acyl, alkyl, cycloalkyl, or cycloalkyl-$C_{1-3}$ alkyl; when n is 0, $R^d$ is hydrogen, alkyl, cycloalkyl, and cycloalkyl-$C_{1-3}$ alkyl and when n is 1 or 2, $R^d$ is alkyl, cycloalkyl, cycloalkyl-$C_{1-3}$ alkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-methoxyethyl, 2-ethoxyethyl, 3-methoxypropyl, 2-aminoethyl, 3-aminopropyl, 2-methylsulfonylethyl, aminosulfonylmethyl, aminosulfonylethyl, aminosulfonylpropyl, methylaminosulfonyl-methyl, methylaminosulfonylethyl, methylaminosulfonylpropyl, and the like.

The term "heterocyclyl" as used herein means a saturated or unsaturated non-aromatic monocyclic or bicyclic radical of 3 to 10 ring atoms in which one or two ring atoms are heteroatom containing groups selected from NR', O, or $S(O)_n$ (where R' is alkyl, heteroalkyl, or hydrogen, and n is an integer from 0 to 2), the remaining ring atoms being carbon. The heterocyclyl radical is optionally substituted with one or more substituents selected from the group consisting of hydroxy, oxo, alkyl, haloalkyl, hydroxyalkyl, heteroalkyl, and acyl. The term heterocyclyl includes, but is not limited to, tetrahydropyranyl, piperidino, tetrahydropyrimidin-5-yl, tetrahydropyrimidin-1-yl, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, tetrahydroquinolin-1-yl and tetrahydroisoquinolin-2-yl, and the like.

The term "arylalkyl" as used herein means a radical —R'R" where R' is an alkylene radical and R" is an aryl radical as defined herein. Examples of arylalkyl radicals include, but are not limited to, 4-fluorophenylmethyl, 3,4-dichlorophenylethyl, and the like.

The term "heteroarylalkyl" as used herein means a radical —R'R" where R' is an alkylene radical and R" is a heteroaryl radical as defined herein. Examples of heteroarylalkyl radicals include, but are not limited to, such as 3-pyridinylmethyl, 4-chloropyrimidin-2-ylmethyl, 2-thiophen-2-ylethyl, and the like.

The term "heterocyclylalkyl" as used herein means a radical —R'R" where R' is an alkylene radical and R" is a heterocyclyl radical as defined herein. Examples of heterocyclylalkyl radicals include, but are not limited to, tetrahydropyran-2-ylmethyl, 2-piperidinylmethyl, 3-piperidinylmethyl, morpholin-1-ylpropyl, and the like.

The term "alkylamino" as used herein means a radical —NR'R", wherein $R^1$ is hydrogen and R" is an alkyl radical as defined herein. The term "dialkylamino" as used herein means a radical —NR'R", wherein R' and R" are alkyl radicals as defined herein. Examples of alkylamino radicals include, but are not limited to, methylamino, ethylamino, cyclopropylmethylamino, dicyclopropylmethylamino, dimethylamino, methylethylamino, diethylamino, di(1-methylethyl)amino, and the like.

The term "acyl" means a formyl radical of the formula —C(O)H, or a carbonyl radical of the formula —C(O)R', where R' is selected from the group consisting of $C_{1-18}$ alkyl, cycloalkyl, cycloalkylalkyl, haloalkyl, heteroalkyl, heterocyclyl, heterocyclylalkyl, aryl, arylalkyl, heteroaryl, heteroarylalkyl, alkoxy, or NR'R", as defined herein, wherein R' and R" are hydrogen or alkyl or R', R" and the nitrogen to which they are attached are a pyrrolidinyl, piperidinyl, morpholinyl, or piperazinyl group.

The term "alkylidenyl" as used herein means a bivalent radical =CRR', wherein R and R' are independently an alkyl radical or hydrogen, as defined herein. Examples of alkylidenyl radicals include, but are not limited to, ethylidenyl, propylidenyl, butylidenyl, and the like.

The term "cycloalkylidenyl" as used herein means a bivalent radical =CRR', wherein R and R' are taken together with the carbon to which they are attached to form a bivalent cycloalkyl radical, as defined herein. Examples of cycloalkylidenyl radicals include, but are not limited to, cyclopentylidenyl, 3-fluorocyclohexylidenyl, and the like.

The term "cycloalkyl-alkylidenyl" as used herein means a bivalent radical =CRR', wherein R is an alkyl radical or hydrogen, and R' is a cycloalkyl radical, as defined herein. Examples of cycloalkyl-alkylidenyl radicals include, but are not limited to, cyclopropylmethylidenyl, cyclohexylmethylidenyl, 1-cyclopentylethylidenyl, and the like.

The term "cycloalkylalkyl-alkylidenyl" as used herein means a bivalent radical =CRR', wherein R is an alkyl radical or hydrogen, and R' is a cycloalkylalkyl radical, as defined herein. Examples of cycloalkylalkyl-alkylidenyl radicals include, but are not limited to, 2-cyclopentylethylidenyl, 1-cyclohexylpropyliden-2-yl, and the like.

The term "heteroalkylidenyl" as used herein means a bivalent radical =CRR', wherein R is an heteroalkyl radical, an haloalkyl radical, an alkyl radical, or hydrogen, and R' is an heteroalkyl radical or an haloalkyl radical, as defined herein. Examples of heteroalkylidenyl radicals include, but are not limited to, 3,3,3-trifluoropropylidenyl, 2-hydroxybutylidenyl, 3-aminopropylidenyl, and the like.

The term "heterocyclylidenyl" as used herein means a bivalent radical =CRR', wherein R and R' are taken together with the carbon to which they are attached to form a bivalent heterocycly! radical, as defined herein. Examples of heterocyclylidenyl radicals include, but are not limited to, pyrrolidinyliden-2-yl, tetrahydropyranyliden-4-yl, piperidinyliden-4-yl, and the like.

The term "heterocyclyl-alkylidenyl" as used herein means a bivalent radical =CRR', wherein R is an alkyl radical or hydrogen, and R' is a heterocyclyl radical, as defined herein. Examples of heterocyclyl-alkylidenyl radicals include, but are not limited to, 4-piperidinylmethylidenyl, 4-methyl-1-piperazinylmethylidene, and the like.

The term "heterocyclylalkyl-alkylidenyl" as used herein means a bivalent radical =CRR', wherein R is an alkyl radical or hydrogen, and R' is a heterocyclylalkyl radical, as defined herein. Examples of heterocyclylalkyl-alkylidenyl radicals include, but are not limited to, 2-(tetrahydropyran-4-yl)ethylidenyl, 1-(piperidin-3-yl)propyliden-2-yl, and the like.

The term "arylalkylidenyl" as used herein means a bivalent radical =CRR', wherein R is an aryl radical, an alkyl radical, or hydrogen, and R' is an aryl radical, as defined herein. Examples of arylalkylidenyl radicals include, but are not limited to, 4-chlorophenylmethylidenyl, 6,7-dimethoxynaphth-2-ylmethylidenyl, and the like.

The term "arylalkyl-alkylidenyl" as used herein means a bivalent radical =CRR', wherein R is an alkyl radical or hydrogen, and R' is an arylalkyl radical, as defined herein. Examples of arylalkyl-alkylidenyl radicals include, but are not limited to, 2-(4-trifluoromethylphenyl)ethylidenyl, 1-(3,4-dichlorophenyl)propyliden-2-yl, and the like.

The term "heteroarylalkylidenyl" as used herein means a bivalent radical =CRR', wherein R is an alkyl radical or hydrogen, and R' is a heteroaryl radical, as defined herein. Examples of heteroarylalkylidenyl radicals include, but are not limited to, 3-pyridinylmethylidenyl, 4-chloro-2-pyrimidinylmethylidenyl, and the like.

The term "heteroarylalkyl-alkylidenyl" as used herein means a bivalent radical =CRR', wherein R is an alkyl radical or hydrogen, and R' is a heteroarylalkyl radical, as defined herein. Examples of heteroarylalkyl-alkylidenyl radicals include, but are not limited to, 2-(4-trifluoromethylpyrimidinyl)ethylidenyl, 1-(thiophen-2-yl)propyliden-2-yl, and the like.

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like.

The term "optional" or "optionally" as used herein means that a subsequently described event or circumstance may, but need not, occur, and that the description includes instances where the event or circumstance occurs and instances in which it does not. For example, "optional bond" means that the bond may or may not be present, and that the description includes single, double, or triple bonds.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al. Angew. Chem. Inter. Edit. 1966, 5, 385; errata 511; Cahn et al. Angew. Chem. 1966, 78, 413; Cahn and Ingold J. Chem. Soc. (London) 1951, 612; Cahn et al. Experientia 1956, 12, 81; Cahn, J. Chem. Educ. 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Atropic isomers" means the isomers owing their existence to restricted rotation caused by hindrance of rotation of large groups about a central bond.

The phrase "substantially pure" as used herein means at least about 90 mole percent of the desired compound, enantiomer or stereoisomer is present compared to other possible configurations.

The phrase "pharmaceutically acceptable" as used herein means that which is useful in preparing a pharmaceutical composition that is generally safe, non-toxic, and neither biologically nor otherwise undesirable and includes that which is acceptable for veterinary as well as human pharmaceutical use.

The phrase "pharmaceutically acceptable salts" of a compound as used herein means salts that are pharmaceutically acceptable, as defined herein, and that possess the desired pharmacological activity of the parent compound. Such salts include:

(i) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (ii) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

The term "crystal forms" or "polymorphs" means crystal structures in which a compound can crystallize in different crystal packing arrangements, all of which have the same elemental composition. Different crystal forms usually have different X-ray diffraction patterns, infrared spectra, melting points, density, hardness, crystal shape, optical and electrical properties, stability and solubility. Recrystallization solvent, rate of crystallization, storage temperature, and other factors may cause one crystal form to dominate.

The term "solvates" as used herein means solvent additions forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the *Mammalia* class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

"Disease state" means any disease, condition, symptom, or indication. "Treating" or "treatment" of a disease state includes: (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms, or (iii) relieving the disease state, i.e., causing temporary or permanent regression of the disease state or its clinical symptoms.

"Mood disorders" or "affective disorders" mean psychopathologic conditions in which a pervasive disturbance of mood constitutes the core manifestation. These terms subsume anxiety and related neuroses, especially the depressive form. Examples of "mood disorders" or "affective disorders" include, but are not limited to, depression, major depressive disorder, single episode depression, recurrent depression, child abuse induced depression, postpartum depression, dysthemia, unipolar disorder, bipolar disorder with manifestations of insomnia and eating disorder, dysthymic disorder, double depression, morbid and clinical depression, mania and cyclothymia.

Nomenclature

In general, the nomenclature used in this Application is based on AUTONOM™ v.4.0, a Beilstein Institute computerized system for the generation of IUPAC systematic nomenclature.

Abbreviations $Ac_2O$ Acetic Anhydride
DME 1,2-dimethoxyethane
DCE 1,2-dichloroethane
THF tetrahydrofuran
TEA triethylamine
rt room temperature
$SiO_2$ silica gel
EtOH ethanol
MeOH methanol
$Et_2O$ diethyl ether
EtOAc ethyl acetate NaNO₂ sodium nitrite
NaOAc sodium acetate
DMSO dimethyl sulfoxide
pTsOH.H₂O p-toluenesulfonic acid monohydrate
Pd(PPh₃)₄(0) tetrakis(triphenyphosphine)palladium(0)
BH₃-THF boron hydride-tetrahydrofuran complex
EDCI 1-(3-dimethylaminopropyl)-3-ethylcarbodimide
HOBT 1-hydroxybenzotriazole hydrate

EXAMPLES OF COMPOUNDS OF THE PRESENT INVENTION

The following examples and preparations are provided to enable those skilled in the art to more clearly understand and to practice the present invention. They should not be considered as limiting the scope of the invention, but merely as being illustrative and representative thereof.

TABLE 1

| Cpd # | Name | Mass spectrum observed (predicted) | mp(° C.) |
|---|---|---|---|
| Ia | 7-(2,4-Dichloro-phenyl)-2-methyl-3-(1-propyl-but-1-enyl)-2H-indazole hydrochloride | 373 (373) | 147–152 |
| Ib | 2-Methyl-3-(1-propyl-but-1-enyl)-7-(2,4,6-trimethyl-phenyl)-2H-indazole hydrochloride | 347 (347) | 132–135 |
| Ic | [2-Methyl-7-(2,4,6-trimethyl-phenyl)-2H-indazol-3-yl]-dipropyl-amine | 350 (350) | 154–158 |
| Id | [7-(2,4-Dichloro-phenyl)-2-methyl-2H-indazol-3-yl]-dipropyl-amine | 376 (376) | 153–157 |
| Ie | (2-Methoxy-ethyl)-[2-methyl-7-(2,4,6-trimethyl-phenyl)-2H-indazol-3-yl]-propyl-amine | 366 (366) | 86–121 |
| If | Bis-(2-methoxy-ethyl)-[2-methyl-7-(2,4,6-trimethyl-phenyl)-2H-indazol-3-yl]-amine | 382 (382) | 140–142 |
| Ig | 3-(3-Methoxy-1-methoxymethyl-propenyl)-7-(4-methoxy-2-methyl-phenyl)-2-methyl-2H-indazole hydrochloride | 367 (367) | oil |
| Ih | Ethyl-(2-methoxy-ethyl)-[2-methyl-7-(2,4,6-trimethyl-phenyl)-2H-indazol-3-yl]-amine hydrochloride | 352 (352) | 142–146 |
| Ii | [7-(4-Methoxy-2-methyl-phenyl)-2-methyl-2H-indazol-3-yl]-dipropyl-amine hydrochloride | 352 (352) | 60–70 |
| Ij | (2-Methoxy-ethyl)-[7-(4-methoxy-2-methyl-phenyl)-2-methyl-2H-indazol-3-yl]-propyl-amine; hydrochloride | 367 (367) | |
| Ik | Cyclopropylmethyl-(2-methoxy-ethyl)-[7-(4-methoxy-2-methyl-phenyl)-2-methyl-2H-indazol-3-yl]-amine hydrochloride | 379 (379) | |
| Il | 7-(2,4-Dimethoxy-phenyl)-2-methyl-3-(1-propyl-but-1-enyl)-2H-indazole hydrochloride | 364 (364) | |
| Im | 2-Methyl-7-(2,4,6-trimethyl-phenyl)-2H-indazole-3-carboxylic acid cyclopropylmethyl-propyl-amide | 390 (390) | 112.5–113.8 |
| In | Cyclopropylmethyl-[2-methyl-7-(2,4,6-trimethyl-phenyl)-2H-indazol-3-ylmethyl]-propyl-amine hydrochloride | 375 (375) | 125.8–133.5 |
| Io | [2-Methyl-7-(2,4,6-trimethyl-phenyl)-2H-indazol-3-yl]-propyl-thiophen-2-ylmethyl-amine trifluoro-acetic acid salt | 404 (404) | |
| Ip | Cyclopropylmethyl-[2-methyl-7-(2,4,6-trimethyl-phenyl)-2H-indazol-3-yl]-propyl-amine trifluoroacetic acid salt | 362 (362) | |
| Iq | Furan-2-ylmethyl-[2-methyl-7-(2,4,6-trimethyl-phenyl)-2H-indazol-3-yl]-propyl-amine trifluoroacetic acid salt | 388 (388) | |
| Ir | Cyclopropylmethyl-[7-(2,4-dichloro-phenyl)-2-methyl-2H-indazol-3-yl]-propyl-amine hydrochloride | 387 (387) | 137.0–139.0 |
| Is | 7-(2,4-Dichloro-phenyl)-2-methyl-2H-indazole-3-carboxylic acid cyclopropylmethyl-propyl-amide | 416 (416) | |
| It | Cyclopropylmethyl-[7-(2,4-dichloro-phenyl)-2-methyl-2H-indazol-3-ylmethyl]-propyl-amine trifluoroacetate | 402 (402) | |
| Iu | [7-(2,4-Dimethoxy-phenyl)-2-methyl-2H-indazol-3-yl]-dipropyl-amine hydrochloride | 368 (368) | 62–64.3 |
| Iv | 4-({[2-Methyl-7-(2,4,6-trimethyl-phenyl)-2H-indazol-3-yl]-propyl-amino}-methyl)-benzonitrile trifluoroacetate | 423 (423) | |
| Iw | 7-(2,4-Dichloro-phenyl)-2-methyl-2H-indazole-3-carboxylic acid bis-(2-methoxy-ethyl)-amide trifluoroacetate | 436 (436) | |
| Ix | [7-(6-Methoxy-2-methyl-pyridin-3-yl)-2-methyl-2H-indazol-3-yl]-dipropyl-amine trifluoroacetate | 353 (353) | |
| Iy | Benzyl-[2-methyl-7-(2,4,6-trimethyl-phenyl)-2H-indazol-3-yl]-propyl-amine trifluoroacetate | 398 (398) | |
| Iz | 7-(6-Methoxy-2-methyl-pyridin-3-yl)-2-methyl-3-((E)-1-propyl-but-1-enyl)-2H-indazole hydrochloride | 350 (350) | 84.7–89.4 |
| Iaa | Dimethyl-{4-methyl-5-[2-methyl-3-((E)-1-propyl-but-1-enyl)-2H-indazol-7-yl]-pyridin-2-yl}-amine trifluoroacetate | 363 (363) | |
| Iab | 7-(2,4-Dichloro-phenyl)-2-ethyl-2H-indazole-3-carboxylic acid cyclopropylmethyl-propyl-amide trifluoroacetate | 430 (430) | |
| Iac | [2-Methyl-7-(2,4,6-trimethyl-phenyl)-2H-indazol-3-yl]-propyl-thiazol-2-ylmethyl-amine trifluoroacetate | 405 (405) | |
| Iad | 7-(2,4-Dichloro-phenyl)-2-methyl-2H-indazole-3-carboxylic acid diethylamide trifluoroacetate | 376 (376) | |
| Iae | [7-(2,4-Dichloro-phenyl)-2-methyl-2H-indazol-3-yl]-morpholin-4-yl-methanone | 390 (390) | 197.0–200.8 |

TABLE 1-continued

| Cpd # | Name | Mass spectrum observed (predicted) | mp(° C.) |
|---|---|---|---|
| Iaf | (3,4-Dimethoxy-benzyl)-[2-methyl-7-(2,4,6-trimethyl-phenyl)-2H-indazol-3-yl]-propyl-amine trifluoroacetate | 458 (458) | |
| Iag | 7-(2,4-Dichloro-phenyl)-2-methyl-3-morpholin-4-ylmethyl-2H-indazole | 376 (376) | 152.3–154.8 |

Compound Preparation

The compounds of Formulae I and II described herein may be prepared by standard synthetic methods. In particular, certain compounds of Formulae I and II may be prepared utilizing as an intermediate 7-bromoindazole (3), the preparation of which is illustrated in Scheme 1. Deprotonation of 3 and N-alkylation of the tautomeric anion with dimethyl sulfate produces a separable mixture of 2-methyl-7-bromoindazole (4) and 1-methyl-7-bromoindazole (18). The $R^3$ (optionally substituted aryl or heteroaryl) substituent can be introduced by standard aryl coupling procedures which are well known in the art. The resulting 7-aryl (or heteroaryl) indazoles, e.g., 4, are readily transformed into the compounds of the present invention as outlined in Schemes 1-3. Similar transformations can be used to convert 18 into the compounds of formula II.

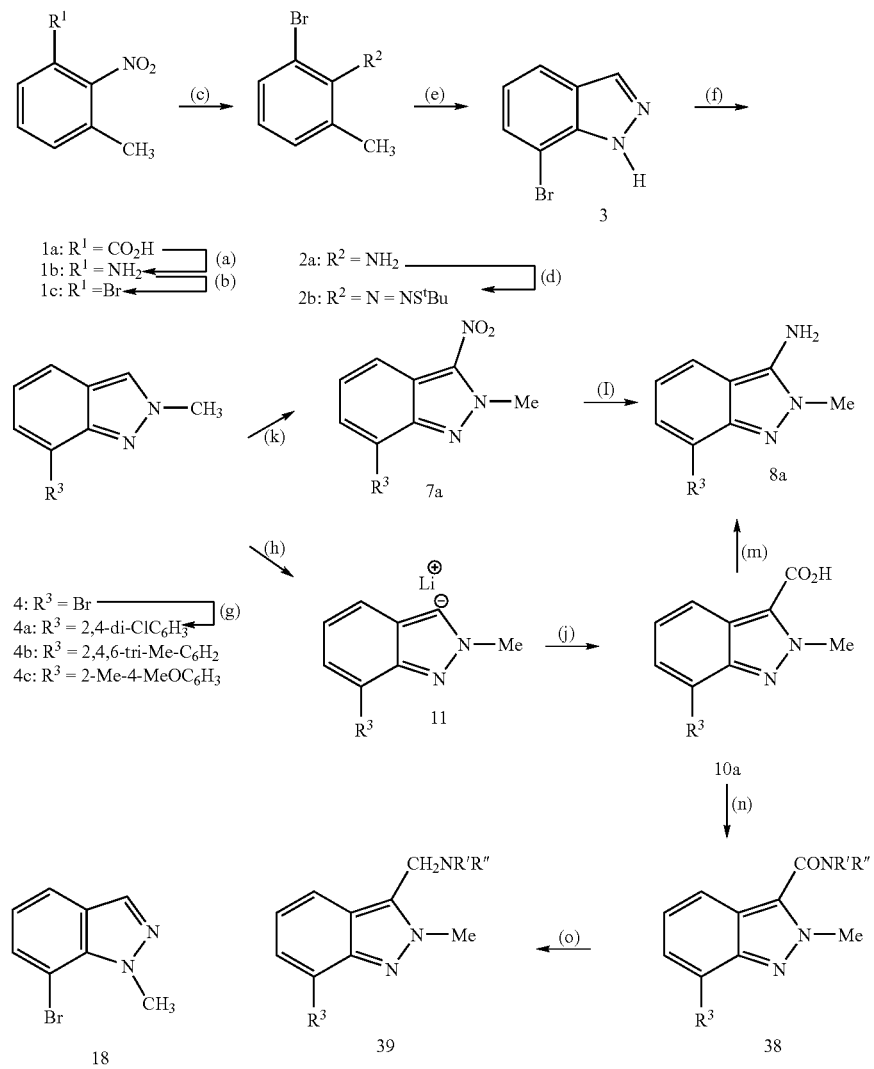

SCHEME 1

(a) NaN$_3$, H$_2$SO$_4$ (67%); (b) t-BuONO, CuBr$_2$, CH$_3$CN, 60° C. (57%); (c) tellurium, NaBH$_4$, EtOH; (d) (i) NaNO$_2$,HCl, H$_2$O (ii) NaOAc, t-BuSH, EtOH; (e) t-BuO$^-$ K$^+$, DMSO, RT (98%); (f) (MeO)$_2$SO$_2$, NaOH, H$_2$O; (g) Pd(PPh$_3$)$_4$(0), Na$_2$CO$_3$, DME, H$_2$O, 2,4-dichlorobenzeneboronic acid, reflux (40%); (h) n-BuLi,THF, −78°; (j) CO$_2$; (k) HNO$_3$, Ac$_2$O; (l) H$_2$, 10% Pd/C, MeOH; (m) (i) (PhO)$_2$PON$_3$, TEA, t-Bu-OH; (ii) TFA, CH$_2$Cl$_2$; (n) HOBT, EDCI, Et$_3$N, HNR'R", CH$_2$Cl$_2$; (o) BH$_3$, THF Nitration of 4a produces a mixture of regioisomeric nitroindazoles from which the 3-nitroindazole 7a is readily isolated. The nitro substituent can be reduced to the corresponding amine 8a under standard conditions. An alternate route to 8a involves treatment of 4a with n-butyllithium to produce the 3-lithiated heterocycle 11 which is quenched with carbon dioxide to produce carboxylic acid 10a. The amine can be prepared from carboxylic acid 10a utilizing the Curtius rearrangement or a variant thereof (J. March Advanced Organic Chemistry 4$^{th}$ Ed J Wiley & Sons: New York, 1991; pp 1090–1095). The carboxylic acid or the corresponding carbocylic ester can be converted into amides of the present invention by condensation protocols well known in the art (see, e.g. Example 8 and 10).

Conversion of amine 8a into amide 12a can be achieved by a variety of methodologies well known in the art (J. March Advanced Organic Chemistry 4$^{th}$ Ed J Wiley & Sons: New York, 1991; pp 417–424 ). Reduction of the amide with borane-THF complex, or other reducing agents, (J. March supra, pp 445–446) affords the secondary amine 13a that can be further transformed to the tertiary amine 15a by reductive amination or via a second acylation and reduction sequence. Alternatively tertiary amines 14a can be prepared directly from 8a by reductive amination. (Scheme 2) The stepwise procedure permits the preparation of tertiary amines with different substituents on the nitrogen atom.

The lithiated heterocycle 11 (Scheme 3) can be quenched with carbonyl compounds to produce carbinols 5 which, in turn, can be dehydrated to olefins 6 described herein. The dehydration produces a mixture of geometrical isomers. The present invention includes both the pure E and Z isomers and mixtures thereof. The olefins optionally can be further converted to the corresponding alkane 17.

SCHEME 2

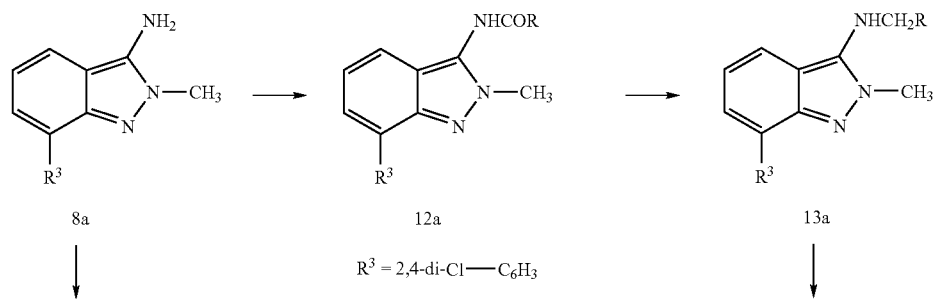

SCHEME 3

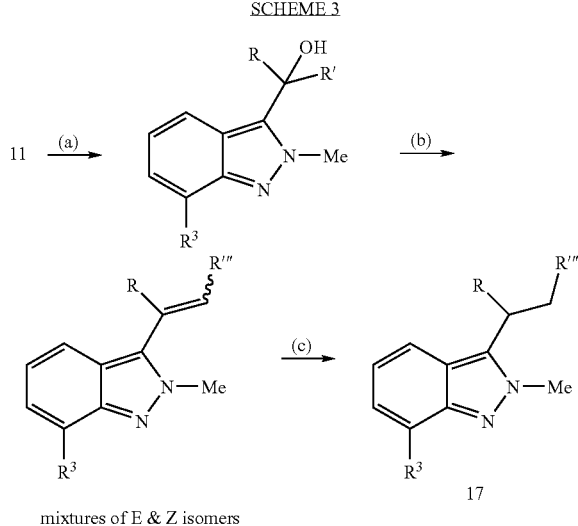

mixtures of E & Z isomers 5
5a: R = R' = n-Pr
    R³ = 2,4-diClC₆H₃
5b: R = R' = n-Pr
    R³ = 2,4,6-triMeC₆H₂

6
6a: R = n-Pr, R'" = Et,
    R³ = 2,4-diClC₆H₃
6b: R = n-Pr, R'" = Et,
    R³ = 2,4,6-triMeC₆H₂

(a)RC (=O)R';(b) p-TsOH, PhCH₃; (c) H₂, Pd/C

Some compounds in Schemes 1–3 are depicted with specific $R^1$, $R^2$ and $R^3$ substituents; however, one skilled in the art will immediately realize that these reactions are also applicable to other compounds contemplated in this invention. Furthermore, the sequence of the synthetic steps can be altered if necessary. Examples 9–11 exemplify incorporation of the aryl group at position by palladium-catalyzed coupling after elaboration of the functionality at the 3-position. The reaction sequences in the following examples are exemplary and are not meant to be limiting.

EXAMPLE 1

7-(2,4-Dichloro-phenyl)-2-methyl-3-(1-propyl-but-1-enyl)-2H-indazole hydrochloride (Ia)

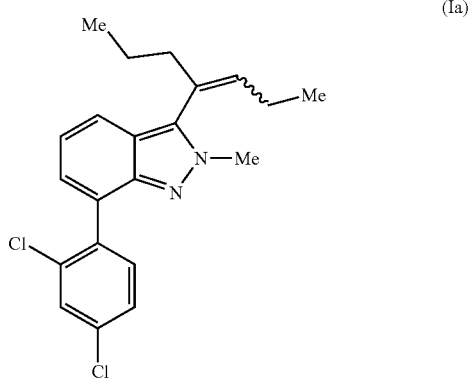

Step 1

3-Bromo-2-nitrotoluene (Scheme 1: 1c)—A mixture of copper(II) bromide (3.52 g, 15.7 mmol) in 20 mL dry acetonitrile was heated to 65° C. under an $N_2$ atmosphere. t-Butyl nitrite (2.35 mL, 2.03 g, 19.7 mmol) was added all at once. A solution of 3-methyl-2-nitroaniline (1b; 2.00 g, 13.1 mmol; *J. Org. Chem.* 1976 41(21):3357) in 15 mL acetonitrile was added to the above solution at a rate to sufficient to maintain gentle reflux. After addition the mixture was heated at a gentle reflux for an additional 15 min. The reaction mixture was cooled to rt and partitioned between 6N HCl solution (150 mL) and ether (150 mL). The ethereal solution was separated and washed with brine, then dried over $MgSO_4$. Evaporation of the solvent afforded 2.76 g of impure material, which was flash chromatographed on $SiO_2$ and eluted with 10% acetone in hexane which afforded 1.62 g (57%) of 1c as a pale yellow-green liquid.

Step 2

2-Bromo-6-methylaniline (2a)—A mixture of tellurium (21.6 g, 169.4 mmol) and $NaBH_4$ (15.0 g, 396 mmol) in 575 mL of absolute EtOH was heated at reflux under an atmosphere of $N_2$ for 1 hr, then allowed to cool to rt. A solution of 3-bromo-2-nitrotoluene (1c; 7.32 g, 33.8 mmol) in 25 mL EtOH was added all at once and the mixture stirred at room temp for 2 hrs. The reaction mixture was filtered through a CELITE® pad and the filtrate evaporated under reduced pressure. The residue was taken up in $Et_2O$ (about 200 mL), washed with brine then dried over $MgSO_4$. Evaporation of the solvent afforded 2.66 g (42%) of 2a as a dark liquid.

Step 3

(2-Bromo-6-methylphenylazo)-t-butylsulfide (2b)—2-Bromo-6-methylaniline (2a; 1.18 g, 6.34 mmol) and 3.4 mL 6N HCl was heated in an oil bath at 60° for 30 min, then cooled to 0°. A solution of $NaNO_2$ (481 mg, 6.97 mmol) in 1.5 mL $H_2O$ was added dropwise then stirred in the cold for an additional hr. The reaction mixture was buffered to a pH between 4 and 5 with saturated NaOAc solution, then added all at once to an ice-cold solution of t-butyl mercaptan (0.80 mL, 629 mg, 6.97 mMol) in 14 mL EtOH. The mixture was allowed to warm to rt overnight. The reaction mixture was partitioned between EtOAc (50 mL) and $H_2O$ (50 mL). The aqueous layer was re-extracted with EtOAc (50 mL). The combined EtOAc extracts were washed with brine and dried over $MgSO_4$. Evaporation of the solvent afforded 1.46 g (80%) of 2b.

Step 4

7-Bromoindazole (3)—A solution of (2-bromo-6-methylphenylazo)-t-butylsulfide (2b; 880 mg, 3.06 mmol) in 10 mL dry DMSO was added dropwise to a solution of potassium t-butoxide (3.44 g, 30.6 mmol) in 25 mL dry DMSO under Ar. The reaction mixture was stirred at room temp for 2 hr, then poured into 150 g ice and 150 mL 2 N HCl solution. The mixture was extracted with ether (2×150 mL). The combined ethereal extracts were washed with brine and dried over $MgSO_4$. Evaporation of the solvent afforded 581 mg (96%) of 3 as a beige solid.

Step 5

7-Bromo-2-methylindazole (4)—A mixture of 7-bromoindazole (3; 576 mg, 2.92 mmol) and NaOH (510 mg, 12.7 mmol) in 15 mL $H_2O$ were heated in an oil bath under $N_2$ atmosphere until the solids dissolved and the resulting solution was cooled to 65° C. Dimethyl sulfate (0.78 mL, 1.03 g, 8.18 mmol) was added and the mixture stirred at 65° for 2 hr. The reaction mixture was cooled to rt and extracted with $CH_2Cl_2$ (2×50 mL). The combined $CH_2Cl_2$ extracts were washed with brine and dried over $Na_2SO_4$. Evaporation of the solvent afforded 775 mg of a mixture of 1-methyl- and 2-methy-7-bromoindazoles which were separated by flash chromatography on SiO$_2$ using EtOAc:hexane (1:2) which afforded 251 mg (45%) of 7-bromo-2-methylindazole (4).

Step 6

7-(2,4-Dichloro-phenyl)-2-methyl-2H-indazole (4a)—7-Bromo-2-methylindazole (4; 251 mg, 1.19 mmol) and Pd(PPh$_3$)$_4$(0) (42 mg, 0.035 mmol) were stirred in 5.5 mL DME under an Ar atmosphere for 30 min. 2,4-Dichlorobenzeneboronic acid (454 mg, 2.38 mmol) was added, followed immediately by 5.25 mL of 2 M Na$_2$CO$_3$ solution. The mixture was heated at a gentle reflux for 2 hr, then cooled to rt and diluted with EtOAc (50 mL). The mixture was then washed with brine and dried over MgSO$_4$. Evaporation of the solvent afforded a dark oil which was flash chromatographed on SiO$_2$ and eluted with EtOAc:hexane (1:2) which afforded 296 mg (90%) of 4a as a colorless viscous liquid.

Step 7

4-[7-(2.4-Dichloro-phenyl)-2-methyl-2H-indazol-3-yl]-heptan-4-ol (5a)—Indazole 4a (292 mg, 1.05 mmol) was dissolved in 5mL dry THF under N$_2$ and cooled to −78°. n-BuLi (0.51 mL of 2.5 M hexane solution, 1.26 mmol) was added dropwise via syringe, then stirred at −78° for 45 min. Heptanone (0.22 mL, 180 mg, 1.58 mmol) was added dropwise and the reaction then allowed to warm to rt. The reaction mixture was diluted with EtOAc (50 mL), washed successively with 50% sat'd. NH$_4$Cl soln and brine, then dried over MgSO$_4$. Evaporation of the organic phase afforded crude material which was flash chromatographed on SiO$_2$ and eluted with EtOAc:hexane (1:3) to afford 152 mg (37%) of 5a.

Step 8

7-(2.4-Dichloro-phenyl)-2-methyl-3-(1-propyl-but-1-enyl)-2H-indazole hydrochloride (Ia; Scheme 3, 6a)—Indazole 5a (220 mg, 0.56 mmol) and pTsOH.H$_2$O (27 mg, 0.14 mmol) were combined in 8 mL dry PhMe under an N$_2$ atmosphere and heated at reflux for 4 hrs. The reaction mixture was cooled to rt, diluted with EtOAc (25 mL) then washed successively with sat'd. NaHCO$_3$ solution and brine, then dried over MgSO$_4$. Evaporation afforded 215 mg of crude product which was flash chromatographed on SiO$_2$ and eluted with EtOAc:hexane (1:4) to afford 195 mg (93%) of the free base of Ia as a viscous oil. The oil was dissolved in Et$_2$O (2 mL) and treated with 1.0 mL of 1.0 M HCl soln in Et$_2$O to afford Ia as a white solid (150 mg; 65%)

EXAMPLE 2

2-Methyl-3-(1-propyl-but-1-enyl)-7-(2,4,6-trimethyl-phenyl)-2H-indazole Hydrochloride (Ib)

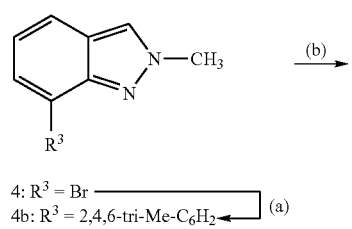

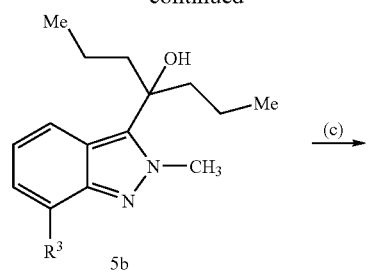

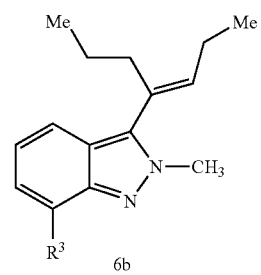

(a) Pd(PPh$_3$)$_4$(0), Na$_2$CO$_3$, DME, H$_2$O, 2,4,6-trimethylphenylboronic acid (53%); (b) (i) n-BuLi, THF, −78°; (ii) 4-heptanone (40%); (c) p-TsOH.H$_2$O, PhMe, reflux (98%)

Step 1

2-Methyl-7-(2,4,6-trimethyl-phenyl)-2H-indazole (4b): 7-Bromo-2-methyl-2H-indazole (4; 0.35 g, 1.66 mMol) and Pd(PPh$_3$)$_4$(0) (58 mg, 0.05 mMol) were stirred in 6 mL DME under argon for 30 min. 2,4,6-Trimethylbenzeneboronic acid (0.54 g, 3.3 mMol) was added, immediately followed by a solution of sodium carbonate (0.62 g, 5.8 mMol) in 5 mL water. The mixture was heated at a gentle reflux for 20 hr, then cooled to rt and diluted with EtOAc (75 mL). The mixture was then washed with brine and dried over MgSO$_4$. Evaporation of the solvent afforded a light yellow solid which was flash chromatography on silica and eluted with hexane:EtOAc (9:1) which afforded 4b as a off-white solid 0.21 g (53%).

Step 2

4-[2-Methyl-7-(2,4,6-trimethyl-phenyl)-2H-indazol-3-yl]-heptan-4-ol (5b; Scheme 1)—Prepared using the procedure of step 7 in Example 1 but substituting 2-methyl-7-(2,4,6-trimethyl-phenyl)-2H-indazole (4b) for 2-methyl-7-(2,4-dichlorophenyl)-2H-indazole.

Step 3

2-Methyl-3-(1-propyl-but-1-enyl)-7-(2,4,6-trimethyl-phenyl)-2H-indazole Hydrochloride (Ib or 6b Scheme 1)—Prepared from 4-[2-Methyl-7-(2,4,6-trimethyl-phenyl)-2H-indazol-3-yl]-heptan-4-ol (5b) using the procedure in step 8 of Example 1.

EXAMPLE 3

3-(3-Methoxy-1-methoxymethyl-propenyl)-7-(4-methoxy-2-methyl-phenyl)-2-methyl-2H-indazole hydrochloride (Ig)

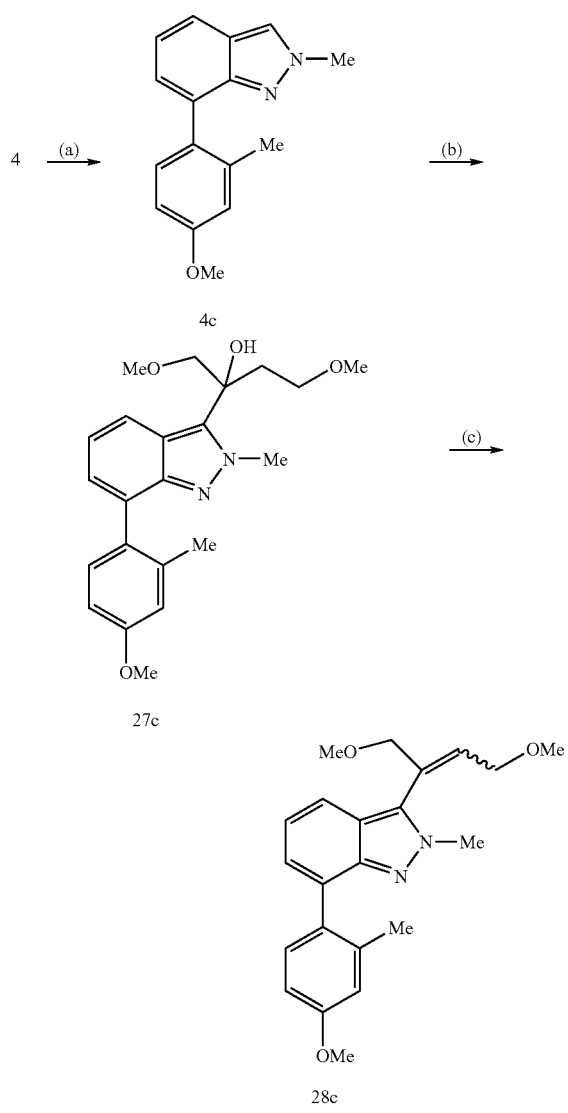

(a) Pd(PPh$_3$)$_4$, Na$_2$CO$_3$, DME, 2-methyl-4-methoxybenzeneboronic acid, reflux, (93%); (b)(i) n-BuLi, THF, −78°; (ii) MeOCH$_2$CO(CH$_2$)$_2$OMe, (65%); (c) p-TsOH.H$_2$O, PhMe, reflux.

Step 1

7-(4-Methoxy-2-methyl-phenyl)-2-methyl-2H-indazole (4c): 7-Bromo-2-methyl-2H-indazole (4; 1.76 g, 8.3 mMol) and tetrakis(triphenylphosphine)palladium(0) (0.28 g, 0.25 mMol) were stirred in 15 mL of DME under argon atmosphere for 30 min. 4-Methoxy-2-methylbenzeneboronic acid (1.52 g, 9.2 mMol) was added, immediately followed by a solution of sodium carbonate (3.1 g, 29.1 mMol) in 10 mL water. The mixture was heated at a gentle reflux for 4 hr, and then cooled to rt and diluted with EtOAc (150 mL). The organic phase was washed with brine and dried over magnesium sulfate. Evaporation of the solvent afforded an oil, which was flash chromatographed on SiO$_2$ and eluted with hexane:EtOAc (9:1) to afford 4c (1.9 g; 91%).

Step 2

1,4-Dimethoxy-2-[7-(4-methoxy-2-methyl-phenyl)-2-methyl-2H-indazol-3-yl]-butan-2-ol (27c): Indazole 4c (0.29 g, 0.79 mMol) was dissolved in 5 mL dry THF under a nitrogen atmosphere and cooled to −78° C. n-BuLi (0.4 mL of 2.5 M hexane solution, 1 mMol) was added dropwise via syringe, and stirred at −78° C. for 10 minutes. 1,4-dimethoxy-2-butanone (0.16 g, 1.18 mMol) was added dropwise at −78° C. and then the reaction mixture was allowed to warm to rt. The reaction mixture was diluted with EtOAc (50 mL) and washed successively with saturated ammonium chloride solution, brine and dried over magnesium sulfate. Evaporation of the solvent afforded crude material which was flash chromatographed on silica and eluted with hexane:EtOAc (3:1) which afforded 27c as an oil (0.196 g; 65%).

Step 3

3-(3-Methoxy-1-methoxymethyl-propenyl)-7-(4-methoxy-2-methyl-phenyl)-2-methyl-2H-indazole hydrochloride (28c or Ig)—Carbinol 27c (0.1 g, 0.26 mMol) and p-TsOH.H$_2$O (25 mg, 0.13 mMol) were combined in 3 mL PhMe under a nitrogen atmosphere and heated at reflux for 2 hr. The reaction mixture was cooled to rt, diluted with EtOAc (25 mL) then washed successively with saturated sodium bicarbonate solution, brine and dried over magnesium sulfate. Evaporation of the solvent afforded the crude product which was flash chromatographed on silica gel and eluted with hexane: EtOAc (4:1) to afford the free base of Ig as an oil (44 mg; 46%). The free-base was dissolved in ether (1.5 mL) and treated with 0.15 mL of 1.0 M HCl solution in ether to afford viscous oil Ig (25 mg).

EXAMPLE 4

[7-(2,4-Dichloro-phenyl)-2-methyl-2H-indazol-3-yl]-dipropyl-amine hydrochloride (Id)

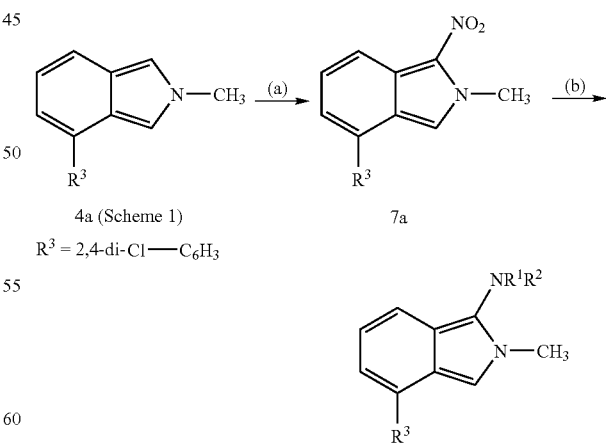

(a) HNO$_3$, Ac$_2$O, HOAc; (b) H$_2$, 10% Pd/C, MeOH; (c) C$_2$H$_5$COCl, TEA, CH$_2$Cl$_2$; (d) BH$_3$THF, THF, reflux; (e) C$_2$H$_5$CHO, Na B(OAc)$_3$H, DCE, rt Step 1

7-(2,4-Dichloro-phenyl)-2-methyl-3-nitro-2H-indazole (7a)—7-(2,4-Dichlorophenyl)-2-methyl-indazole (4a Scheme 1; 293 mg, 1.05 mmol) was dissolved in 3.0 mL of glacial HOAc and 0.3 mL of acetic anhydride then cooled in an ice bath. 90% Nitric acid (0.070 mL; 1.48 mmol) was added all at once and allowed to stir at rt for 1 hr, then heated in an oil bath at 50° for 2 hr. The 10 reaction mixture was cooled to rt then treated with ice (~10 g). The mixture was extracted with ether (2×40 mL). The combined ethereal extracts were washed with sat'd NaHCO$_3$ soln (2×50 mL), then dried over MgSO$_4$. Evaporation afforded a mixture of 3 isomers which were separated by silica gel flash chromatography (EtOAc:hexane, 1:9) which afforded 77 mg (22%) of 7a.

Step 2

7-(2,4-Dichloro-phenyl)-2-methyl-2H-indazol-3-ylamine (8a)—Nitroindazole 7a and 10 mg of 10% Pd on C were combined in 7 mL of MeOH then stirred under a hydrogen atmosphere (1 atm) overnight. Filtration of the catalyst and evaporation of the solvent afforded 70 mg of 8a, which was used in the next step without further purification.

Step 3

N-[7-(2,4-Dichloro-phenyl)-2-methyl-2H-indazol-3-yl]-propionamide (22a)—Amine 8a (70 mg, 0.23 mmol) and TEA (0.037 mL, 26 mg, 0.26 mmol) were dissolved in methylene chloride (3 mL) under a N$_2$ atmosphere and cooled in an ice bath. Propionyl chloride (0.022 mL, 24 mg, 0.26 mmol) was added and then allowed to warm to room temp. When the reaction was complete, the mixture was evaporated and the residue flash chromatographed (ethyl acetate:hexane, 1:1) to afford 68 mg (82%) of 22a.

Step 4

[7-(2,4-Dichloro-phenyl)-2-methyl-2H-indazol-3-yl]-propyl-amine (23a)—Amide 22a (68 mg, 0.19 mmol) was dissolved in 5 mL dry THF under a N$_2$ atmosphere. A 1M BH$_3$-THF solution (0.40 mL, 0.40 mmol) was added all at once and the mixture heated at reflux for 2 hr, cooled to rt and 1 mL 6N HCl was cautiously added, and the mixture was reheated at reflux for 1 hr, and then cooled to rt. The mixture was made basic with 6N NaOH solution, then extracted with methylene chloride (2×25 mL). The combined extracts were washed with brine and dried over Na$_2$SO$_4$. Evaporation of the solvent afforded 71 mg of 23a as a light brown viscous liquid, which was used without further purification.

Step 5

[7-(2,4-Dichloro-phenyl)-2-methyl-2H-indazol-3-yl]-dipropyl-amine hydrochloride (24a or Id)—Amine 23a and propionaldehyde (0.032 mL, 26 mg, 0.44 mmol) were combined in 3 mL of DCE under nitrogen and allowed to stir at rt for 10 min. Na(OAc)$_3$BH (102 mg, 0.48 mmol) was added all at once and the reaction mixture stirred at rt overnight. The reaction mixture was diluted with 20 mL methylene chloride and washed with dilute NH$_4$OH solution. The CH$_2$Cl$_2$ solution was separated and dried (Na$_2$SO$_4$). Evaporation of the solvent afforded a residue which was purified by flash chromatography (EtOAc:hexane, 1:9) to afford 27.4 mg of the free base of Id as a viscous liquid. The free base was dissolved in 1 mL ether and treated with 0.1 mL 2M HCl in ether solution which afforded 22 mg of Id as a white solid.

The following compounds were similarly prepared according to Example 4

Cyclopropylmethyl-[2-methyl-7-(2,4,6-trimethyl-phenyl)-2H-indazol-3-yl]-propyl-amine trifluoroacetic acid salt (Ip)

Furan-2-ylmethyl-[2-methyl-7-(2,4,6-trimethyl-phenyl)-2H-indazol-3-yl]-propyl-amine trifluoroacetic acid salt (Iq)

[2-Methyl-7-(2,4,6-trimethyl-phenyl)-2H-indazol-3-yl]-propyl-thiophen-2-ylmethyl-amine trifluoro-acetic acid salt (Io)

EXAMPLE 5

[2-Methyl-7-(2,4,6-trimethyl-phenyl)-2H-indazol-3-yl]-dipropyl-amine hydrochloride (Ic)

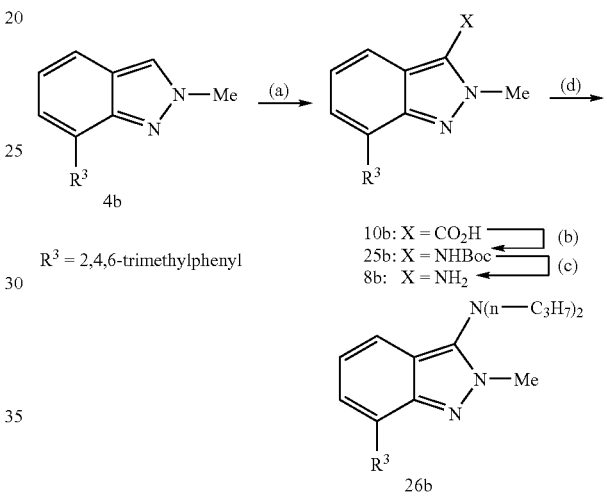

(a)(i) n-Bu Li, THF, (ii) CO$_2$, −78° C., (69%); (b) (C$_6$H$_5$O)$_2$P(O)N$_3$, Et$_3$N, t-BuOH (49%); (c) TFA, CH$_2$Cl$_2$, rt, (90%); (d) C$_2$H$_5$CHO, Na(AcO)$_3$BH, DCE, rt, (82%)

Step 1

2-Methyl-7-(2,4,6-trimethyl-phenyl)-2H-indazole-3-carboxylic acid (10b)—2-Methyl-7-(2,4,6-trimethyl-phenyl)-2H-indazole (4b; 0.31 g, 1.2 mMol) was dissolved in 5 mL dry THF under nitrogen and cooled to −78° C. n-BuLi (0.7 mL of 2.5 M hexane solution, 1.75 mMol) was added dropwise via syringe, stirred at −78° C. for 15 minutes. The temperature was raised to −40° C. and stirred for 30 minutes. The reaction was cooled to −78° C. and dry carbon dioxide gas was bubbled into the reaction mixture for 5 minutes, then the reaction mixture was warmed to room temperature. The reaction mixture was quenched with 10% HCl solution, extracted with EtOAc (50 mL), washed with brine and dried over magnesium sulfate. Evaporation afforded light yellow solid, treated with ether, filtered, dried to afford the title compound as an off-white solid 0.24 g (10b, 69%).

Step 2

[2-Methyl-7-(2,4,6-trimethyl-phenyl)-2H-indazol-3-yl]-carbamic acid tert-butyl ester (25b)—2-Methyl-7-(2,4,6-trimethyl-phenyl)-2H-indazole-3-carboxylic acid (10b; 0.64 g, 2.17 mMol) was combined with 3.0 mL of t-butanol and 0.6 mL of TEA was added. To the mixture was added 0.6 mL of diphenylphosphoryl azide and the reaction mixture was heated to 85° C. for 6 hr. After cooling to rt, the reaction mixture was diluted in EtOAc (25 mL) and washed with 1M aqueous sodium bisulfate, aqueous sodium bicarbonate, water, and brine. The EtOAc solution was dried with magnesium sulfate and concentrated to give material which was chromatographed on silica eluting with hexane:EtOAc (9:1) to afford 0.39 g (49%) of 25b as an off-white solid.

Step 3

2-Methyl-7-(2,4,6-trimethyl-phenyl)-2H-indazol-3-ylamine (8b)—To a solution of [2-methyl-7-(2,4,6-trimethyl-phenyl)-2H-indazol-3-yl]-carbamic acid tert-butyl ester (25b, 0.35 g, 0.96 mMol) in 10 mL of dichloromethane, was added 5 mL of trifluoroacetic acid at room temperature and stirred for 20 hours. The reaction mixture was then diluted with $CH_2Cl_2$ and washed with dilute aqueous $NH_4OH$. The aqueous phase was washed with additional $CH_2Cl_2$, after which the combined extracts were dried with magnesium sulfate and concentrated to afford 8b as an off-white solid (0.23 g; 90%).

Step 4

[2-Methyl-7-(2,4,6-trimethyl-phenyl)-2H-indazol-3-yl]-dipropyl-amine Hydrochloride (26b or Ic)—To a solution of 2-methyl-7-(2,4,6-trimethyl-phenyl)-2H-indazol-3-ylamine (8b, 0.23 g, 0.86 mMol) in 15 mL of DCE was added propionaldehyde (0.2 mL, 0.16 g, 2.77 mMol) followed a few minutes later by sodium triacetoxyborohydride (0.64 g, 3.02 mMol). The reaction mixture was stirred at room temperature for 2 days, during which time an additional 0.3 mL of propionaldehyde and an additional 0.64 g of sodium triacetoxyborohydride were added. The mixture was then diluted with dichloromethane and washed with dilute aqueous $NH_4OH$. The organic phase was dried over magnesium sulfate and concentrated. The residue was chromatographed on silica gel eluting with an ethyl acetate/hexane gradient to provide the free base of Ic as a dark pink solid 0.175 g (58%). The free base was dissolved in 3 mL ether and treated with 0.5 mL of 1.0 M HCl solution in ether to afford Ic as an off-white solid (142 mg).

EXAMPLE 6

Preparation of (2-Methoxy-ethyl)-[2-methyl-7-(2,4,6-trimethyl-phenyl)-2H-indazol-3-yl]-propyl-amine Hydrochloride (Ie); and, Ethyl-(2-methoxy-ethyl)-[2-methyl-7-(2,4,6-trimethyl-phenyl)-2H-indazol-3-yl]-amine Hydrochloride (Ih)

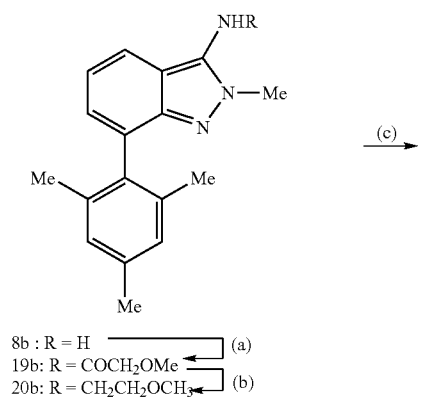

8b : R = H
19b: R = COCH₂OMe
20b: R = CH₂CH₂OCH₃

(a)
(b)

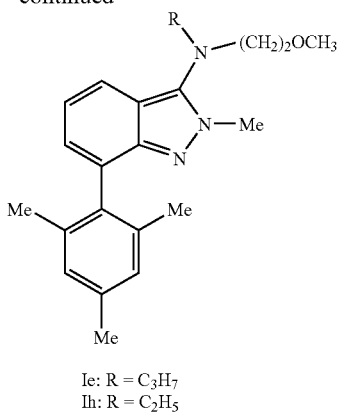

Ie: R = C₃H₇
Ih: R = C₂H₅

(a) MeOCH₂CH₂COCl, Et₃N, THF (78%); (b) BH₃.THF, THF (47%); (c)R'CHO, Na(AcO)₃BH, DCE, rt, (51%)

Step 1

2-Methoxy-N-[2-methyl-7-(2,4,6-trimethyl-phenyl)-2H-indazol-3-yl]-acetamide (19b)-2-Methyl-7-(2,4,6-trimethyl-phenyl)-2H-indazol-3-ylamine (8b; 0.17 g, 0.64 mmol) and TEA (0.09 mL, 0.065 g, 0.66 mMol) were dissolved in dry THF (6 mL) under nitrogen atmosphere and cooled in an ice bath. Methoxyacetyl chloride (0.06 mL, 0.071 g, 0.66 mMol) was added and reaction mixture allowed to warm to rt and stirred for 2 hours. The reaction was quenched with cold water, diluted with ethyl acetate and washed with saturated sodium bicarbonate solution, brine and dried over magnesium sulfate. The organic phase was concentrated to afford 19b as a light pink solid (0.16 g; 78%).

Step 2

(2-Methoxy-ethyl)-[2-methyl-7-(2,4,6-trimethyl-phenyl)-2H-indazol-3-yl]-amine (20b)—2-Methoxy-N-[2-methyl-7-(2,4,6-trimethyl-phenyl)-2H-indazol-3-yl]-acetamide (19b; 0.16 g, 0.47 mMol) was dissolved in 7 mL dry THF under a nitrogen atmosphere. A 1M solution of borane-THF complex in THF (0.95 mL, 0.95 mMol) was added all at once and the mixture heated at reflux for 2 hours, then cooled to rt. The reaction mixture was then acidified with 10% HCl aqueous solution and extracted with ethyl acetate (2×50 mL). The combined extracts were washed with 1M NaOH, water, brine, and dried over magnesium sulfate. The solvent was evaporated and the residue was flash chromatographed on silica eluting with hexane: acetone (9:1) to afford 20b as a light yellow semi-solid (0.072 g; 47%).

Step 3

(2-Methoxy-ethyl)-[2-methyl-7-(2,4,6-trimethyl-phenyl)-2H-indazol-3-yl]-propyl-amine hydrochloride (Ie)—To a solution of (2-methoxy-ethyl)-[2-methyl-7-(2,4,6-trimethyl-phenyl)-2H-indazol-3-yl]-amine (20b, 47 mg, 0.15 mMol) in 4 mL of DCE was added propionaldehyde (0.03 mL, 0.024 g, 0.42 mMol) followed a few minutes later by sodium triacetoxyborohydride (0.11 g, 0.52 mMol). The reaction was stirred at room temperature for four hours, then diluted with dichloromethane and washed with dilute aqueous ammonium hydroxide. The organic layer was dried over magnesium sulfate and concentrated. The residue was chromatographed on silica and eluted with an acetone/hexane gradient to provide the free base of the title compound as an oil (28 mg; 51%). The free base was dissolved in 1 mL ether and treated with 0.1 mL of 1.0 M HCl solution in ether to afford Ie as a light yellow powder (20 mg).

Ethyl-(2-methoxy-ethyl)-[2-methyl-7-(2,4,6-trimethyl-phenyl)-2H-indazol-3-yl]-amine Hydrochloride (Ih)—To a solution of (2-methoxy-ethyl)-[2-methyl-7-(2,4,6-trimethyl-phenyl)-2H-indazol-3-yl]-amine (20b, 0.113 g, 0.35 mMol) in five mL of dichloroethane was added acetaldehyde (0.07 mL, 0.055 g, 1.25 mMol) followed a few minutes later by sodium triacetoxyborohydride (0.26 g, 1.23 mMol). The reaction mixture was stirred at room temperature for four hours, then diluted with dichloromethane and washed with dilute aqueous ammonium hydroxide. The organic phase was dried over magnesium sulfate and the solvent evaporated. The residue was chromatographed on silica gel and eluted with an acetone/hexane gradient to provide the free base of the title compound as an oil (72 mg; 58%). The free base was dissolved in 3 mL ether and treated with 0.25 mL of 1.0 M HCl solution in ether to afford Ih as a pink powder hydrochloride (65 mg).

EXAMPLE 7

Bis-(2-methoxy-ethyl)-[2-methyl-7-(2,4,6-trimethyl-phenyl-2H-indazol-3-yl]-amine hydrochloride (If)

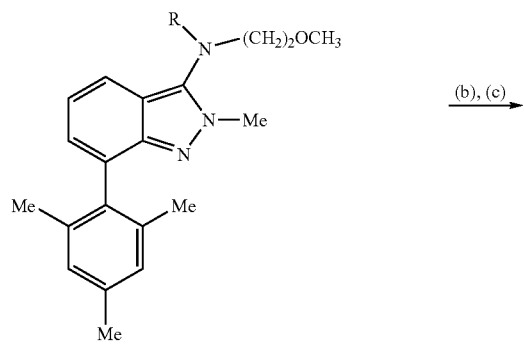

20b: R = H
21b: R = COCH$_2$OME

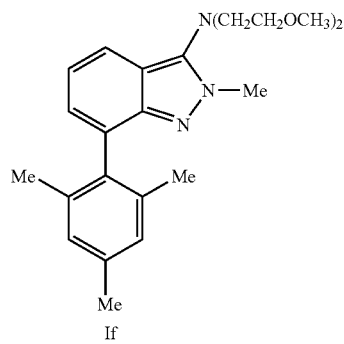

If (a) MeOCH$_2$COCl, TEA, THF (89%); (b) BH$_3$ THF THF, reflux; (c) HCl, Et$_2$O (68%)

Step 1

2-Methoxy-N-(2-methoxy-ethyl)-N-[2-methyl-7-(2,4,6-trimethyl-phenyl)-2H-indazol-3yl]-acetamide (21b)—(2-Methoxy-ethyl)-[2-methyl-7-(2,4,6-trimethyl-phenyl)-2H-indazol-3-yl]-amine (20b, 72 mg, 0.22 mMol) and TEA (0.033 mL, 0.024 g, 0.24 mMol) were dissolved in dichloromethane (3 mL) under a nitrogen atmosphere and cooled in an ice bath. Methoxyacetyl chloride (0.02 mL, 0.024 g, 0.24 mMol) was added and the reaction mixture allowed to warm to rt and stirred for two hr. Reaction mixture was quenched with cold water, diluted with dichloromethane and washed with saturated aqueous sodium bicarbonate solution, brine and dried over magnesium sulfate. The solvent was evaporated to afford 70 mg (80%) of 21b as an oil.

Step 2

Bis-(2-methon-ethyl)-[2-methyl-7-(2,4,6-trimethyl-phenyl)-2H-indazol-3-yl]-amine hydrochloride (If)—2-Methoxy-N-(2-methoxy-ethyl)-N-[2-methyl-7-(2,4,6-trimethyl-phenyl)-2H-indazo-3-yl]-acetamide (21b, 70 mg, 0.18 mMol) was dissolved in 5mL of dry THF under nitrogen. A 1.0 M solution of BH$_3$-THF complex (0.35 mL, 0.35 mMol) was added all at once and the mixture heated at reflux for 2 hr, then cooled to rt. The reaction mixture was acidified with 10% HCl aqueous solution and extracted with EtOAc (2×25mL) The organic phase was washed with 1M NaOH, water, brine, dried over magnesium sulfate and concentrated. The residue was flash chromatographed on silica and eluted with hexane:acetone (9: 1) to afford the free base of If as an oil 46 mg (68%). The free base was dissolved in 2 mL ether and treated with 0.14 mL of 1.0 M HCl solution in ether to afford If as a white powder (25 mg).

EXAMPLE 8

2-Methyl-7-(2,4,6-trimethyl-phenyl)-2H-indazole-3-carboxylic acid cyclopropylmethyl-propyl-amide (Im) and Cyclopropylmethyl-[2-methyl-7-(2,4,6-trimethyl-phenyl)-2H-indazol-3-ylmethyl]-propyl-amine hydrochloride (In)

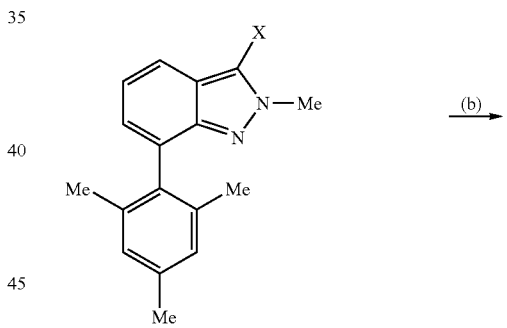

10b: X = CO$_2$H
Im : X = CON(Pr)CH$_2$—c—C$_3$H$_5$

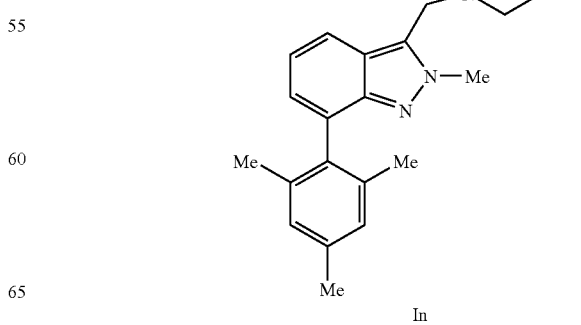

In (a) HOBT, EDCI, Et₃N, CH₂Cl₂, c-C₃H₅CH₂NH-n-Pr, rt (66%); (b) BH3 THF, THF, reflux (76%).

2-Methyl-7-(2,4,6-trimethyl-phenyl)-2H-indazole-3-carboxylic acid cyclopropylmethyl-propyl-amide (Im)—2-Methyl-7-(2,4,6-trimethylphenyl)indazole-3 carboxylic acid (10b; 400 mg, 1.35 mmol), 1-hydroxybenzotriazole hydrate (202 mg, 1.49 mmol), 1-(3-dimethylaminopropyl)-3-ethyl-carbodimide (EDCI ) (287 mg, 1.49 mmol), TEA (0.38 mL, 275 mg, 2.71 mmol), and N-propyl-N-cyclopropylmethy-lamine (0.20 mL, 153 mg, 1.35 mmol) were combined in 16 mL CH₂Cl₂ under an N₂ atmosphere and stirred for five hr at rt. The reaction mixture was diluted with EtOAc (50 mL), washed successively with 1N HCl, H₂O, and saturated NaHCO₃, and then dried over MgSO₄. Evaporation of the solvent afforded 486 mg of crude product, which was flash chromatographed (EtOAc:hexane, 1:3) to afford 350 mg (66%) of a viscous liquid , which crystallized on standing to a white solid. (Im; mp 112.5°–113.8°)

Cyclopropylmethyl-[2-methyl-7-(2,4,6-trimethyl-phenyl)-2H-indazol-3-ylmethyl]-propyl-amine hydrochloride (In)—(N-Cyclopropylmethyl-N-propyl)-2-methyl-7-(2,4,6-trimethylphenyl) indazole-3-carboxamide (Im; 263 mg, 0.67 mmol) and 1M borane-THF solution (1.35 mL, 1.35 mmol) were combined in 10 mL of dry THF under a N₂ atmosphere and heated at reflux overnight. A 2N HCl soln (4 mL) was added cautiously and heated at reflux for 20 min, then allowed to cool in an ice bath. The mixture was made basic with 6N NaOH soln, then partitioned between EtOAc (30 mL) and brine (25 mL). The EtOAc layer was separated and dried over MgSO₄. Evaporation of the solvent afforded a residue which was flash chromatographed (1:3 EtOAc: hexane) to afford 193 mg (76%) as a viscous liquid which crystallized on standing. The free base was converted to an off-white solid dihydrochloride salt. (In; mp 125.8°–133.5°)

EXAMPLE 9

[7-(6-Methoxy-2-methyl-pyridin-3-yl)-2-methyl-2H-indazol-3-yl]-dipropyl-amine trifluoroacetate

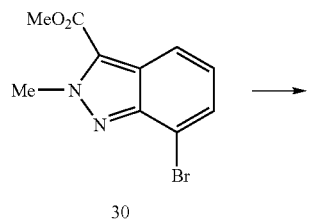

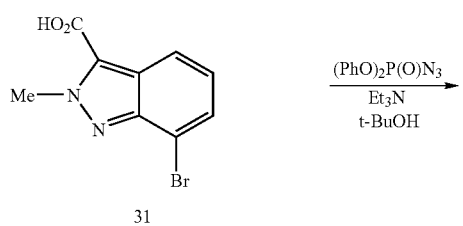

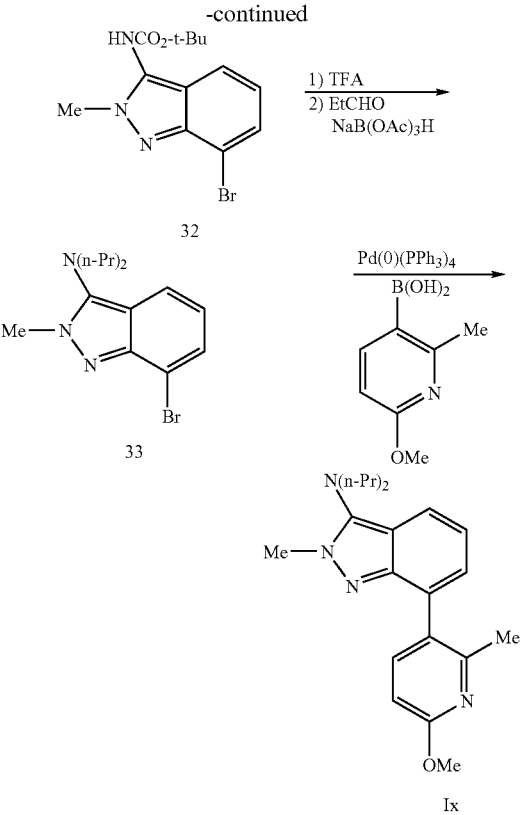

Step 1

7-Bromo-2-methyl-2H-indazole-3-carboxylic acid (31)—A solution of 7-bromo-2-methyl-2H-indazole-3-carboxylic acid methyl ester (30; 3.37 g, 12.5 mmol), 60 mL of methanol, 20 mL of water, and lithium hydroxide monohydrate (1.61 g, 38.4 mmol) was stirred at 67° C. for 16.5 h, then concentrated to remove methanol. The residue was partitioned between 50 mL of water and 50 mL of dichloromethane. The aqueous layer was washed with 50 mL of dichloromethane and acidified with 3 mL of a concentrated aqueous HCl solution. The precipitated solid was isolated by filtration, rinsing well with water, and dried in vacuo affording 2.52 g (79%) of 7-bromo-2-methyl-2H-indazole-3-carboxylic acid (31) as a pale yellow solid, which was used without further purification.

Step 2

(7-bromo-2-methyl-2H-indazol-3-yl)-carbamic acid tert-butyl ester (32)—A solution of 7-bromo-2-methyl-2H-indazole-3-carboxylic acid (31; 2.51 g, 9.84 mmol), 25 mL of toluene, 25 ml of tert-butanol, triethylamine (4.2 mL, 30 mmol), and diphenylphosphoryl azide (6.4 mL, 30 mmol) was stirred for 1 h at room temperature, then heated to 100° C. and stirred for 28 h. After the solution had cooled, 50 mL of ethyl acetate were added, and the solution was sequentially washed with 50 mL of water and 50 mL of a saturated aqueous NaCl solution, dried over MgSO₄, filtered, and concentrated to a yellow oil. Column chromatography (0→33% EtOAc/hexanes) afforded 2.80 g (87%) of 32 as a pale yellow solid.

Step 3

(7-bromo-2-methyl-2H-indazol-3-yl)-dipropyl-amine (33)—To a solution of (7-bromo-2-methyl-2H-indazol-3-yl)-carbamic acid tert-butyl ester (32; 0.092 g, 0.28 mmol) in 2.8 mL of dichloromethane was added 1.5 mL of trifluoroacetic acid. The solution was stirred for 5 h, then quenched with a 1 M aqueous NaOH solution. The mixture was extracted with three 10 mL portions of dichloromethane. The combined organic layers were dried over MgSO$_4$, filtered, and concentrated to 0.072 g (>100%) of crude 7-bromo-2-methyl-2H-indazol-3-ylamine. To this crude 7-bromo-2-methyl-2H-indazol-3-ylamine was added 7 mL of dichloroethane and propionaldehyde (0.072 mL, 0.99 mmol), and the mixture was stirred for 10 min. Sodium triacet-oxyborohydride (0.237 g, 1.12 mmol) was added, and the mixture was stirred for 3 h. Additional propionaldehyde (0.097 mL, 1.3 mmol) was added, the mixture was stirred for 20 min., then additional sodium triacetoxyborohydride (0.320 g, 1.51 mmol) was added and the mixture was stirred for 19 h. Additional propionaldehyde (0.074 mL, 1.0 mmol) was added, the mixture was stirred for 1 h, then additional sodium triacetoxyborohydride (0.250 g, 1.18 mmol) was added and the mixture was stirred for 4 h. The mixture was partitioned between dichloromethane and a 1 M aqueous NaOH solution, and the aqueous layer was extracted with three 50 mL portions of dichloromethane. The combined organic layers were dried over MgSO$_4$, filtered, and concentrated to a brown oil. Column chromatography (0→10% EtOAc/hexanes) afforded 0.062 g (62%) of (7-bromo-2-methyl-2H-indazol-3-yl)-dipropyl-amine (33).

Step 4

[7-(6-Methoxy-2-methyl-pyridin-3-yl)-2-methyl-2H-indazol-3-yl]-dipropyl-amine trifluoroacetate (Ix)—A mixture of (7-bromo-2-methyl-2H-indazol-3-yl)-dipropyl-amine (0.062 g, 0.20 mmol), tetrakis(triphenylphosphine) palladium(0) (0.014 g, 0.012 mmol), 4-methoxy-2-methyl-3-pyridyl boronic acid (0.040 g, 0.24 mmol), 1 mL of N,N-dimethylformamide and 0.4 mL of a 2 M aqueous K$_3$PO$_4$ solution was stirred at 65° C. for 8.5 h. Solvents were removed in vacuo and the crude mixture was purified by reverse-phase HPLC to afford Ix.

EXAMPLE 10

7-(2,4-Dichloro-phenyl)-2-methyl-2H-indazole-3-carboxylic acid cyclopropylmethyl-propyl-amide

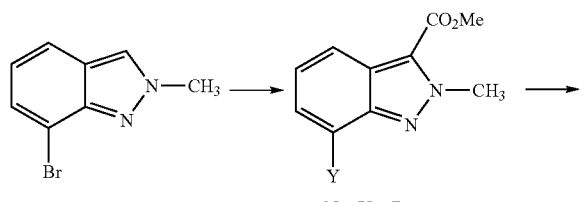

34

35a: Y = Br
35b: Y = Ar

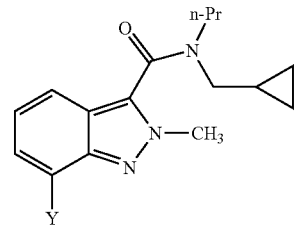

Is: Y = 2,4-dichlorophenyl

Step 1

7-Bromo-2-methyl-2H-indazole-3-carboxylic acid methyl ester (35a)—To a solution of 7-bromo-2-methyl-2H-indazole (34; 1.50 g, 7.12 mmol) in 50 mL of THF at −78° C. was added a 2 M solution of lithium diisopropylamide (LDA) in THF/heptane/ethylbenzene (4.3 mL, 8.6 mmol). The solution was stirred at 0–5° C. for 15 min, then rechilled to −78° C. To the solution was added methyl chloroformate (0.66 mL, 8.5 mmol) all at once, and the mixture was stirred while slowly warm to room temperature over 19 h. The reaction was quenched with silica gel and concentrated. Column chromatography (0→20% EtOAc/hexanes) afforded of 7-bromo-2-methyl-2H-indazole-3-carboxylic acid methyl ester (35a: 1.52 g; 79%; m.p. 131–132) as a pale yellow solid.

Step 2

7-(2.4-Dichloro-phenyl)-2-methyl-2H-indazole-3-carboxylic acid methyl ester (35b)—A mixture of 35a (0.750 g, 2.79 mmol), 2,4-dichlorophenyl boronic acid (1.06 g, 5.57 mmol), 10 mL of ethylene glycol dimethyl ether, tetrakis (triphenylphosphine) palladium(0) (0.097 g, 0.084 mmol), and 10 mL of a 2 M aqueous Na$_2$CO$_3$ solution was stirred at 85° C. overnight, then allowed to cool. Ethyl acetate (50 mL) was added, and the mixture was washed with 30 mL of a saturated aqueous NaCl solution, dried over MgSO$_4$, filtered, and concentrated to a yellow oil. Column chromatography (0→10% EtOAc/hexanes) afforded of 7-(2,4-dichloro-phenyl)-2-methyl-2H-indazole-3-carboxylic acid methyl ester (35b: 0.582 g; 62%; m.p. 128–131) as a white solid.

Step 3

7-(2,4-dichloro-phenyl)-2-methyl-2H-indazole-3-carboxylic acid cyclopropylmethyl-propyl-amide (Is)—To a solution of N-propylcyclopropanemethyl amine (0.69 mL, 4.8 mmol) in 12 mL of benzene was slowly added a 2M solution of trimethylaluminum in heptane (2.4 mL, 4.8 mmol), and the solution was stirred for 75 min. The solution was transferred with a pipette to a solution of 35b (0.200 g, 0.597 mmol) in 10 mL of benzene. The solution was heated to 79° C., stirred for 2 d, then cooled to 0–5° C. A 2 M aqueous NaOH solution (20 mL) was slowly added, and the mixture was extracted with three 20 mL portions of dichloromethane. The combined organic layers were washed with 40 mL of a saturated NaCl solution, dried over MgSO$_4$, filtered, and concentrated to a brown oil. Column chromatography (0→20% EtOAc/hexanes) afforded Is (0.117 g; 47%) as an oil.

The following compounds were similarly prepared according to Example 10:
7-(2,4-dichloro-phenyl)-2-methyl-2H-indazole-3-carboxylic acid bis-(2-methoxy-ethyl)-amide trifluoroacetate (Iw)
7-(2,4-dichloro-phenyl)-2-methyl-2H-indazole-3-carboxylic acid diethylamide trifluoroacetate (Iad)
[7-(2,4-dichloro-phenyl)-2-methyl-2H-indazol-3-yl]-morpholin-4-yl-methanone (Iae)

The following compound was similarly prepared according to Example 10 except 7-bromo-2-ethylindazole was used in the reaction sequence and prepared as in Example 1 step 5 substituting diethyl sulfate for dimethyl sulfate
7-(2,4-dichloro-phenyl)-2-ethyl-2H-indazole-3-carboxylic acid cyclopropylmethyl-propyl-amide trifluoroacetate (Iab).

EXAMPLE 11

7-(2,4-Dichloro-phenyl)-2-methyl-3-((E)-1-propyl-but-1-enyl)-2H-indazole

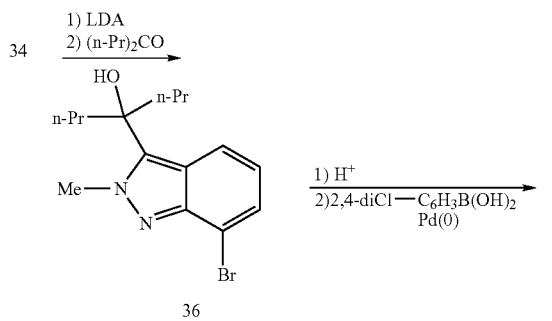

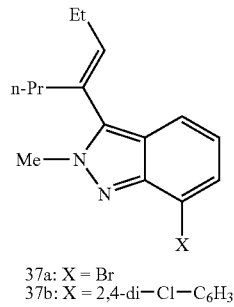

37a: X = Br
37b: X = 2,4-di—Cl—C$_6$H$_3$

Step 1
4-(7-bromo-2-methyl-2H-indazol-3-yl)-heptan-4-ol (36)—To a solution of 7-bromo-2-methyl-2H-indazole (34; 1.5 g, 7.1 mmol) in 18 mL of tetrahydrofuran (THF) at −78° C. was added a 2 M solution of LDA in THF/heptane/ethylbenzene (5.3 mL, 11 mmol). The solution was stirred at 0–5° C. for 10 m, then rechilled to −78° C. To the solution was added 4-heptanone (1.49 mL, 10.6 mmol), and the solution was stirred overnight, allowing to slowly warm to rt. A saturated aqueous NaHCO$_3$ solution (40 mL) was added, and the mixture was extracted with three 30 mL portions of ethyl acetate. The combined organic layers were dried over Na$_2$SO$_4$, filtered, and concentrated to a brown solid. Column chromatography (0→20% EtOAc/hexanes) afforded 1.80 g (78%) of 36.

Step 2
7-bromo-2-methyl-3-((E)-1-propyl-but-1-enyl)-2H-indazole (37a)—A solution of 4-(7-bromo-2-methyl-2H-indazol-3-yl)-heptan-4-ol (36; 1.75 g, 5.38 mmol), 50 mL of toluene, and 4-toluenesulfonic acid (1.23 g, 6.46 mmol) was stirred at 110° C. for 20 h, then allowed to cool. A saturated aqueous NaHCO$_3$ solution (50 mL) was added, and the mixture was extracted with three 30 mL portions of ethyl acetate. The combined organic layers were dried over MgSO$_4$, filtered, and concentrated to a brown oil. Column chromatography (0→8% EtOAc/hexanes) afforded 1.47 g (89%) of 37a.

Step 3
7-(2,4-dichloro-phenyl)-2-methyl-3-((E)-1-propyl-but-1-enyl)-2H-indazole (37b)—A mixture of 7-bromo-2-methyl-3-((E)-1-propyl-but-1-enyl)-2H-indazole (37a; 1.47 g, 4.79 mmol), 2,4-dichlorophenyl boronic acid (1.32 g, 6.94 mmol), 18 mL of ethylene glycol dimethyl ether, tetrakis(triphenylphosphine)palladium(0) (0.166 g, 0.143 mmol) and 20 mL of a 2 M aqueous Na$_2$CO$_3$ solution was stirred at 85° C. overnight, then allowed to cool. Ethyl acetate (50 mL) was added, and the mixture was washed with two 40 mL portions of a saturated aqueous NaCl solution. The combined aqueous layers were extracted with 20 mL of ethyl acetate. The combined organic layers were dried over Na$_2$SO$_4$, filtered, and concentrated to a brown oil. Column chromatography (0→5% EtOAc/hexanes) afforded 1.57 g (88%) of 7-(2,4-dichloro-phenyl)-2-methyl-3-((E)-1-propyl-but-1-enyl)-2H-indazole (37b) as a white solid.

EXAMPLE 12

Pharmaceutical Compositions

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (IV) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

EXAMPLE 13

Intracellular cAMP Stimulation Assay

Human Y-79 retinoblastoma cells are grown in RPMI 1640 medium with 15% FBS. Measures of cAMP accumulation are performed by using NEN Adenylyl Cyclase Flash-Plate kit (SMP004). The cells are separated from culture medium, washed twice with PBS (150×g, 8 min), resuspended (2E+6 cells/ml) in Stimulation Buffer (provided in the kit), and then added to 96-well FlashPlates, (50,000 cells per well). Various concentrations of test compounds are incubated with the cells for 20 min prior to the addition of hCRF (30 nM). The total assay volume is 100 µl. The assay is terminated after 20 min after addition of the hCRF by addition of Detection Buffer and [$^{125}$I]cAMP. After 2 hr at room temperature the mixtures are aspirated and the bound radioactivity is measured with a Packard TopCount. The potency ($IC_{50}$ values) of test compounds in inhibiting the hCRF-stimulated accumulation of cAMP is determined by nonlinear regression analyses with interactive curve-fitting procedures.

EXAMPLE 14

CRF Receptor Binding Assay

Human IMR-32 neuroblastoma cells are grown to 80% confluence in MEM medium containing 10% heat-inactivated FBS, 1mM Sodium Pyruvate, and 0.1 mM nonessential amino acids. Cell membranes are prepared according the method of Dieterich and DeSouza (1996). The cells (~5E+9) are resuspended in 10 volumes of wash buffer (5 mM Tris HCl, 10 mM $MgCl_2$, 2 mM EGTA, pH 7.4 at RT), homogenized with a Polytron, and then centrifuged at 45,000 G for 20 min at 4° C. The membrane pellets are washed twice with wash buffer (45,000 G for 20 min at 4° C.) and then resuspended (50 mM Tris HCl, 10 mM $MgCl_2$, 2 mM EGTA, pH 7.4 at RT). Protein concentration is determined using Pierce reagents and BSA as standard. Aliquots of 1–1.5 mL are stored at −80° C. until binding assay.

The competition binding assay is performed in a final volume of 250 µl, which contains assay buffer (50 mM Tris-HCl, 10 mM $MgCl_2$, 2 mM EGTA, 0.2% BSA, 0.1 mM bacitracin and 100 kIU/mL aprotinin pH 7.2 at rt), 0.05 nM [$^{125}$I]Tyr$^0$-ovine CRF (Du Pont New England Nuclear), 50 µg of membrane protein, and test compound at various concentrations. Non-specific binding is determined with 1 uM hCRF. Binding reactions are terminated after 2 hr incubation at 25° C. by filtering through 96-w GF/C filter plate using a Packard Harvester (Filtermate 196). The 96-w filter plate is pre-treated with 0.3% polyethyleneimine and pre-washed with washing buffer (50 mM Tris-HCl, 10 mM $MgCl_2$, 2 mM EGTA, 0.2% BSA, pH 7.2 at 4° C.). Unbound radioactivity is removed by four rapid washes (0.8 ml/well) with wash buffer. The radioactivity is quantified using a Packard TopCount. Data are analyzed using non-linear iterative curve fitting to obtain $IC_{50}$ and Hill slope values. PKi values are derived from $pIC_{50}$ values ($-\log$ of $IC_{50}$).

The compounds of the present invention were active in receptor binding and functional assays. The $pIC_{50}$ of representative examples in the CRF1 functional assay are shown in Table 2,

TABLE 2

| Compound | hCRF1 $pIC_{50}$ |
|---|---|
| Ia | 7.2 |
| Ib | 7.3 |
| Ic | 7.1 |
| Io | 7.1 |
| Ip | 7.3 |

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula I:

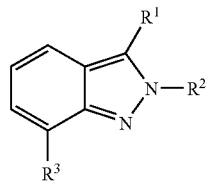

(I)

wherein:
$R^1$ is $-NR^aR^b$, $-CR^cR^dR^e$, $CO_2R^a$, or $-C(O)NR^aR^b$; or $R^1$ is cycloalkenyl, aryl, or heteroaryl, where each aryl or heteroaryl is optionally substituted with one or more substituents independently selected from $C_{1-6}$ alkyl, $C_{1-6}$ alkoxy, $C_{1-6}$ alkylthio, $C_{1-6}$ alkylsulfonyl, halogen, haloalkyl, cyano, nitro, $-C(O)NR^{a\prime}R^{b\prime}$, and $-NR^{a\prime}R^{b\prime}$, where $R^{a\prime}$ and $R^{b\prime}$ are each independently selected from the group consisting of hydrogen, $C_{1-9}$ alkyl, and $C_{1-9}$ alkylcarbonyl4 and with the proviso that $R^1$ can not be 4-methoxyphenyl when $R^3$ is unsusbtituted phenyl;

$R^2$ is hydrogen, $C_{1-6}$ alkyl, $C_{3-6}$ cycloalkyl, $C_{3-6}$ cycloalkyl-$C_{1-3}$ alkyl, $C_{1-6}$ alkylcarbonyl, $C_{1-6}$ alkylsulfonyl, aryl, or arylalkyl, wherein said aryl or arylalkyl is optionally substituted with one or more substituents independently selected from $C_{1-6}$ alkyl, haloalkyl, $C_{1-6}$ alkoxy, and halogen;

$R^3$ is aryl or heteroaryl, each optionally substituted with one or more substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and $-NR^{a\prime\prime}R^{b\prime\prime}$, where $R^{a\prime\prime}$ and $R^{b\prime\prime}$ are each independently selected from the group consisting of hydrogen, $C_{1-9}$ alkyl, and $C_{1-9}$ alkylcarbonyl;

$R^a$ and $R^b$ are each independently selected from the group consisting of hydrogen, $C_{1-9}$ alkyl, hydroxyalkyl, $C_{1-6}$ alkoxyalkyl, $C_{1-6}$ alkylthioalkyl, carboxyalkyl, acyl, $C_{3-6}$ cycloalkyl, $C_{3-6}$ cycloalkyl-$C_{1-3}$ alkyl, di-$C_{3-6}$ cycloalkyl$C_{1-3}$ alkyl, $C_{1-6}$ heteroalkyl, aminoalkyl, aminocarbonylalkyl, cyanoalkyl, $C_{5-8}$ heterocyclyl, heterocyclylalkyl, aryl, arylalkyl, heteroaryl, heteroarylalkyl, phenylalkyl, diphenylalkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or $R^a$ and $R^b$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$ alkyl, haloalkyl, $C_{1-6}$ alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group, pyrrolidin-1-yl, piperidin-1-yl, morpholin-1-yl and piperazin-1-yl;

$R^c$ is hydrogen, hydroxy, $C_{1-6}$ alkoxy, or $-NR^{a\prime\prime\prime}R^{b\prime\prime\prime}$;

$R^d$ and $R^e$ are each independently selected from the group consisting of hydrogen, $C_{1-9}$ alkyl, hydroxyalkyl, $C_{1-6}$ alkoxyalkyl, $C_{1-6}$ alkylthioalkyl, heteroalkyl, heterocyclyl, heterocyclylalkyl, $C_{3-6}$ cycloalkyl, $C_{3-6}$ cycloalkyl-$C_{1-3}$ alkyl, di-$C_{3-6}$ cycloalkyl-$C_{1-3}$ alkyl, aryl, arylalkyl, heteroaryl, heteroarylalkyl, phenylalkyl, diphenyl-$C_{1-3}$alkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, and halogen; or $R^c$ and $R^d$ are taken together to form a divalent group selected from $C_{1-6}$ alkylidenyl, $C_{1-6}$ heteroalkylidenyl, $C_{3-6}$ cycloalkylidenyl, $C_{3-6}$ cycloalkyl-alkylidenyl, $C_{3-6}$ cycloalkyl-$C_{1-3}$ alkyl-alkylidenyl, $C_{3-6}$ heterocyclylidenyl, $C_{3-6}$ heterocyclyl-$C_{1-3}$ alkylidenyl, $C_{3-6}$ heterocyclylalkyl-$C_{1-3}$ alkylidenyl, aryl-$C_{1-3}$ alkylidenyl, aryl-$C_{1-3}$ alkyl-alkylidenyl, heteroaryl-$C_{1-3}$ alkylidenyl, and heteroarylalkyl-$C_{1-3}$ alkylidenyl, wherein each of said cycloalkyl, aryl, or heteroaryl groups is optionally substituted with one or more substituents independently selected from $C_{1-6}$ alkyl, haloalkyl, $C_{1-6}$ alkoxy, amino, alkylamino, dialkylamino, and halogen; or $R^d$ and $R^e$ are taken together with the carbon to which they are attached to form a cycloalkyl or heterocyclyl ring;

$R^{a'''}$ and $R^{b'''}$ are each independently selected from the group consisting of hydrogen, $C_{1-9}$ alkyl, hydroxyalkyl, $C_{1-6}$ alkoxyalkyl, $C_{1-6}$ alkylthioalkyl, carboxyalkyl, acyl, $C_{3-6}$ cycloalkyl, $C_{3-6}$ cycloalkyl-$C_{1-3}$ alkyl, di-$C_{3-6}$ cycloalkyl-$C_{1-3}$ alkyl, $C_{1-6}$ heteroalkyl, aminoalkyl, aminocarbonylalkyl, cyanoalkyl, $C_{5-8}$ heterocyclyl, heterocyclylalkyl, aryl, arylalkyl, heteroaryl, heteroarylalkyl, phenylalkyl, diphenyl-$C_{1-3}$ alkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or $R^{a'''\ and\ Rb'''}$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$ alkyl, haloalkyl, $C_{1-6}$ alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group;

or individual stereoisomers, racemic or non-racemic mixtures of stereoisomers, or pharmaceutically acceptable salts thereof.

2. The compound of claim 1 wherein $R^3$ is optionally substituted phenyl.

3. The compound of claim 2, wherein $R^3$ is a di- or tri-substituted phenyl.

4. The compound of claim 3, wherein $R^3$ is a 2,4-disubstituted or 2,4,6-trisubstituted phenyl.

5. The compound of claim 4, wherein $R^3$ is a 2,4-disubstituted or 2,4,6-trisubstituted phenyl, and the substituents are each independently selected from the group consisting of $C_{1-6}$ alkyl, $C_{1-6}$ alkoxy, $C_{1-6}$ alkylthio, halogen, haloalkyl, cyano, alkylamino, dialkylamino, and nitro.

6. The compound of claim 5, wherein $R^2$ is hydrogen, $C_{1-6}$ alkyl, or $C_{1-6}$ alkylcarbonyl.

7. The compound of claim 3, wherein $R^1$ is —$CR^cR^dR^e$ and $R^c$ is hydroxy.

8. The compound of claim 7, wherein $R^d$ and $R^e$ are each independently selected from the group consisting of hydrogen, $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally substituted with one or more substituents independently selected from the group consisting of $C_{1-6}$ alkyl, haloalkyl, $C_{1-6}$ alkoxy, and halogen.

9. The compound of claim 7, wherein $R^d$ and $R^e$ are each independently selected from the group consisting of $C_{1-9}$ alkyl, $C_{1-6}$ alkoxyalkyl, aryl, and heteroaryl, where each of said aryl or heteroaryl groups is optionally substituted with one or more substituents independently selected from the group consisting of $C_{1-6}$ alkyl, haloalkyl, $C_{1-6}$ alkoxy, and halogen.

10. The compound of claim 9, wherein $R^2$ is $C_{1-6}$ alkyl; and $R^3$ is a 2,4-disubstituted or 2,4,6-trisubstitut phenyl, and the substituents are each independently selected from the group consisting of $C_{1-6}$ alkyl, $C_{1-6}$ alkoxy, halogen, haloalkyl, cyano, and —$NR^{a''}R^{b''}$, where $R^{a''}$ and $R^{b''}$ are each independently selected from the group consisting of hydrogen and $C_{1-9}$ alkyl.

11. The compound of claim 7, wherein $R^d$ and $R^e$ are taken together to form a cycloalkyl or heterocyclyl group.

12. The compound of claim 3, wherein $R^1$ is —$CR^cR^dR^e$; $R^e$ is selected from the group consisting of $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally substituted with one or more substituents independently selected from the group consisting of $C_{1-6}$ alkyl, haloalkyl, $C_{1-6}$ alkoxy, and halogen; and $R^c$ and $R^d$ are taken together to form a divalent group selected from $C_{1-6}$ alkylidenyl, $C_{1-6}$ heteroalkylidenyl, $C_{3-6}$ cycloalkylidenyl, $C_{3-6}$ cycloalkyl-alkylidenyl, $C_{3-6}$ cycloalkyl-$C_{1-3}$ alkyl-alkylidenyl, $C_{3-6}$ heterocyclylidenyl, $C_{3-6}$ heterocyclyl-$C_{1-3}$ alkylidenyl, $C_{3-6}$ heterocyclylalkyl-$C_{1-3}$ alkylidenyl, aryl-$C_{1-3}$ alkylidenyl, aryl-$C_{1-3}$ alkyl-alkylidenyl, heteroaryl-$C_{1-3}$ alkylidenyl, and heteroarylalkyl-$C_{1-3}$ alkylidenyl, wherein each of said cycloalkyl, aryl, or heteroaryl groups is optionally substituted.

13. The compound of claim 12, wherein $R^c$ and $R^d$ are taken together to form a divalent group selected from $C_{1-6}$ alkylidenyl, $C_{3-6}$ cycloalkyl-alkylidenyl, aryl-$C_{1-3}$ alkylidenyl, and heteroaryl-$C_{1-3}$ alkylidenyl, wherein each of said aryl or heteroaryl groups is optionally substituted.

14. The compound of claim 3, wherein $R^1$ is —$CR^cR^dR^e$; $R^e$ is selected from the group consisting of $C_{1-9}$ alkyl, $C_{1-6}$ alkoxyalkyl, and heteroaryl, where the heteroaryl is optionally substituted with one or more substituents independently selected from the group consisting of $C_{1-6}$ alkyl, haloalkyl, $C_{1-6}$ alkoxy, and halogen; and $R^c$ and $R^d$ are taken together to form a divalent group selected from $C_{1-6}$ alkylidenyl, $C_{3-6}$ cycloalkyl-alkylidenyl, $C_{3-6}$ heterocyclyl-$C_{1-3}$ alkylidenyl, aryl-$C_{1-3}$ alkylidenyl, and heteroaryl-$C_{1-3}$ alkylidenyl, wherein each of said aryl, or heteroaryl groups is optionally substituted with one or more substituents independently selected from $C_{1-6}$ alkyl, $C_{1-6}$ alkoxy, amino, alkylamino, and dialkylamino.

15. The compound of claim 3, wherein $R^1$ is —$CR^cR^dR^e$ and $R^c$ is hydrogen.

16. The compound of claim 15, wherein $R^d$ and $R^e$ are each independently selected from the group consisting of $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally substituted with one or more substituents independently selected from the group consisting of $C_{1-6}$ alkyl, haloalkyl, $C_{1-6}$ alkoxy, and halogen.

17. The compound of claim 15, wherein $R^d$ and $R^e$ are each independently selected from the group consisting of $C_{1-9}$ alkyl, $C_{1-6}$ alkoxyalkyl, aryl, and heteroaryl, where each of said aryl or heteroaryl groups is optionally substituted with one or more substituents independently selected from the group consisting of $C_{1-6}$ alkyl, haloalkyl, $C_{1-6}$ alkoxy, and halogen; $R^2$ is $C_{1-6}$ alkyl; and $R^3$ is a 2,4-disubstituted or 2,4,6-trisubstituted phenyl, and the substituents are independently selected from the group consisting of $C_{1-6}$ alkyl, $C_{1-6}$ alkoxy, halogen, haloalkyl, cyano, and —$NR^{a''}R^{b''}$, where $R^{a''}$ and $R^{b''}$ are each independently selected from the group consisting of hydrogen and $C_{1-9}$ alkyl.

18. The compound of claim 3, wherein $R^1$ is —$NR^{a''}R^b$; —$C(O)NR^aR^b$; or —$CR^cR^dR^e$, where $R^c$ is —$NR^{a'''}R^{b\propto''}$ and $R^d$ and $R^e$ are each independently selected from the group consisting of hydrogen $C_{1-9}$alkyl.

19. The compound of claim 18, wherein $R^a$, $R^b$, $R^{a'''}$, and $R^{b''''}$ are independently selected from the group consisting of hydrogen, $C_{1-9}$ alkyl, hydroxyalkyl, $C_{1-6}$ alkoxyalkyl, $C_{3-6}$ cycloalkyl-$C_{1-3}$ alkyl, heterocyclylalkyl, optionally substituted arylalkyl, and optionally substituted heteroarylalkyl.

20. The compound of claim 18, wherein $R^a$ and $R^b$, or $R^{a'''}$ and $R^{b''''}$, are taken together with the nitrogen to which they are attached form an heterocyclyl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, and imidazoline, where each of said rings is optionally substituted with one or more substituents independently selected from the group consisting of hydroxy, oxo, alkyl, aminoalkyl, acyl, acylamino, aminocarbonyl, aminocarbonylalkyl, and aminocarbonylamino, and each of said amino groups is optionally monosubstituted or disubstituted with alkyl, or is contained in a pyrrolidinyl, piperidinyl, morpholinyl, or piperazinyl group.

21. The compound of claim 3, wherein
$R^1$ is —$NR^aR^b$;
$R^a$ is selected from the group consisting of hydrogen, $C_{1-9}$ alkyl, and $C_{1-6}$ alkoxyalkyl; and,
$R^b$ is selected from the group consisting of $C_{1-9}$ alkyl, hydroxyalkyl, $C_{1-6}$ alkoxyalkyl, $C_{3-6}$ cycloalkyl-$C_{1-3}$ alkyl, heterocyclylalkyl, arylalkyl, and heteroarylalkyl, wherein each of said aryl or heteroaryl groups is optionally substituted.

22. The compound of claim 21, wherein $R^2$ is $C_{1-6}$ alkyl; and R3 is a 2,4-disubstituted or 2,4,6-trisubstituted phenyl, and the substituents are independently selected from the group consisting of $C_{1-6}$ alkyl, $C_{1-6}$ alkoxy, halogen, haloalkyl, cyano, and —$NR^{a''}R^{b''}$, where $R^{a''}$ and $R^{b''}$ are each independently selected from the group consisting of hydrogen and $C_{1-9}$ alkyl.

23. The compound of claim 3 wherein
$R^1$ is —$CR^cR^dR^e$;
$R^c$ is $NR^{a'''}R^{b'''}$;
$R^d$ and $R^e$ are each independently selected from the group consisting of hydrogen and $C_{1-9}$ alkyl;
$R^{a'''}$ is selected from the group consisting of hydrogen, $C_{1-9}$ alkyl, and $C_{1-6}$ alkoxyalkyl; and,
$R^{b'''}$ is selected from the group consisting of $C_{1-9}$ alkyl, hydroxyalkyl, $C_{1-6}$ alkoxyalkyl, $C_{3-6}$ cycloalkyl-$C_{1-3}$ alkyl, heterocyclylalkyl, arylalkyl, and heteroarylalkyl, wherein each of said aryl or heteroaryl groups is optionally substituted.

24. The compound of claim 23, wherein $R^2$ is $C_{1-6}$ alkyl; and $R^3$ is a 2,4-disubstituted or 2,4,6-trisubstituted phenyl, and the substituents are independently selected from the group consisting of $C_{1-6}$ alkyl, $C_{1-6}$ alkoxy, halogen, haloalkyl, cyano, and —$NR^{a''}R^{b''}$, where $R^{a''}$ and $R^{b''}$ are each independently selected from the group consisting of hydrogen and $C_{1-9}$ alkyl.

25. The compound of claim 3, wherein $R^1$ is aryl or heteroaryl, where said aryl or heteroaryl is optionally substituted with one or more substituents independently selected from $C_{1-6}$ alkyl, $C_{1-6}$ alkoxy, $C_{1-6}$ alkylthio, $C_{1-6}$ alkylsulfonyl, halogen, haloalkyl, cyano, nitro, and —$NR^{a'}R^{b'}$, where and $R^{a'}$ and $R^{b'}$ are each independently selected from the group consisting of hydrogen, $C_{1-9}$ alkyl, and $C_{1-9}$ alkylcarbonyl.

26. The compound of claim 25, where said aryl or heteroaryl is optionally substituted with one or more substituents independently selected from $C_{1-6}$ alkyl, $C_{1-6}$ alkoxy, halogen, haloalkyl, cyano, and —$NR^{a'}R^{b'}$, where $R^{a'}$ and $R^{b'}$ are each independently selected from the group consisting of hydrogen, $C_{1-9}$ alkyl, and $C_{1-9}$ alkylcarbonyl.

27. The compound of claim 1 wherein $R^3$ is an optionally substituted pyridinyl.

28. The compound of claim 1, wherein $R^3$ is a di- or tri-substituted pyridinyl.

29. The compound of claim 27, wherein $R^1$ is —$CR^cR^dR^e$ and $R^c$ is hydroxy.

30. The compound of claim 29, wherein $R^d$ and $R^e$ are each independently selected from the group consisting of hydrogen, $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally substituted with one or more substituents independently selected from the group consisting of $C_{1-6}$ alkyl, haloalkyl, $C_{1-6}$ alkoxy, and halogen.

31. The compound of claim 30, wherein $R^d$ and $R^e$ are each independently selected from the group consisting of $C_{1-9}$ alkyl, $C_{1-6}$ alkoxyalkyl, aryl, and heteroaryl, where each of said aryl or heteroaryl groups is optionally substituted with one or more substituents independently selected from the group consisting of $C_{1-6}$ alkyl, haloalkyl, $C_{1-6}$ alkoxy, and halogen.

32. The compound of claim 29, wherein $R^d$ and $R^e$ are taken together to form a cycloalkyl or heterocyclyl group.

33. The compound of claim 27, wherein $R^1$ is —$CR^cR^d R^e$; $R^e$ is selected from the group consisting of $C_{1-9}$ alkyl, $C_{1-6}$ alkoxyalkyl, $C_{3-6}$ cycloalkyl, $C_{3-6}$ cycloalkyl-$C_{1-3}$ alkyl, aryl, arylalkyl, heteroaryl, and heteroarylalkyl, where each of said aryl or heteroaryl groups is optionally substituted with one or more substituents independently selected from the group consisting of $C_{1-6}$ alkyl, haloalkyl, $C_{1-6}$ alkoxy, and halogen; and $R^c$ and $R^d$ are taken together to form a divalent group selected from $C_{1-6}$ alkylidenyl, $C_{1-6}$ heteroalkylidenyl, $C_{3-6}$ cycloalkylidenyl, $C_{3-6}$ cycloalkyl-alkylidenyl, $C_{3-6}$ cycloalkyl-$C_{1-3}$ alkyl-alkylidenyl, $C_{3-6}$ heterocyclylidenyl, C_{3-6} heterocyclyl-C_{1-3} alkylidenyl, C_{3-6} heterocyclylalkyl-C_{1-3} alkylidenyl, aryl-C_{1-3} alkylidenyl, aryl-C_{1-3} alkyl-alkylidenyl, heteroaryl-C_{1-3} alkylidenyl, and heteroarylalkyl-C_{1-3} alkylidenyl, wherein each of said cycloalkyl, aryl, or heteroaryl groups is optionally substituted.

34. The compound of claim 33, wherein $R^c$ and $R^d$ are taken together to form a divalent group selected from C_{1-6} alkylidenyl, C_{3-6} cycloalkyl-alkylidenyl, aryl-C_{1-3} alkylidenyl, and heteroaryl-C_{1-3} alkylidenyl.

35. The compound of claim 33, wherein $R^1$ is —CR^cR^dR^e; $R^e$ is selected from the group consisting of C_{1-9} alkyl, C_{1-6} alkoxyalkyl, and heteroaryl, where the heteroaryl is optionally substituted with one or more substituents independently selected from the group consisting of C_{1-6}alkyl, haloalkyl, C_{1-6} alkoxy, and halogen; and $R^c$ and $R^d$ are taken together to form a divalent group selected from C_{1-6} alkylidenyl, C_{3-6} cycloalkyl-alkylidenyl, C_{3-6} heterocyclyl-C_{1-3} alkylidenyl, aryl-C_{1-3} alkylidenyl, and heteroaryl-C_{1-3} alkylidenyl, wherein each of said aryl, or heteroaryl groups is optionally substituted with one or more substituents independently selected from C_{1-6} alkyl, C_{1-6} alkoxy, amino, alkylamino, and dialkylamino.

36. The compound of claim 27, wherein $R^1$ is —CR^cR^dR^e and $R^c$ is hydrogen.

37. The compound of claim 36, wherein $R^d$ and $R^e$ are each independently selected from the group consisting of C_{1-9} alkyl, C_{1-6} alkoxyalkyl, C_{3-6} cycloalkyl, C_{3-6} cycloalkyl-C_{1-3} alkyl, aryl, arylalkyl, heteroaryl, and heteroarylalkyl, where each of said aryl or heteroaryl groups is optionally substituted with one or more substituents independently selected from the group consisting of C_{1-6} alkyl, haloalkyl, C_{1-6} alkoxy, and halogen.

38. The compound of claim 27, wherein $R^1$ is —NR^aR^b; —C(O)NR^aR^b; or —CR^cR^dR^e, where $R^c$ is —NR^{a'''}R^{b'''}; and, $R^d$ and $R^e$ are each independently selected from the group consisting of hydrogen and C_{1-9}alkyl.

39. The compound of claim 38, wherein $R^a$, $R^b$, $R^{a'''}$, and $R^{b'''}$ are each independently selected from the group consisting of hydrogen, C_{1-9} alkyl, hydroxyalkyl, C_{1-6} alkoxyalkyl, C_{3-6} cycloalkyl-C_{1-3} alkyl, heterocyclylalkyl, arylalkyl, and heteroarylalkyl.

40. The compound of claim 38, wherein $R^a$ and $R^b$, or $R^{a'''}$ and $R^{b'''}$, are taken together with the nitrogen to which they are attached form an heterocyclyl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, and imidazoline, where each of said rings is optionally substituted with one or more substituents independently selected from the group consisting of hydroxy, oxo, alkyl, aminoalkyl, acyl, acylamino, aminocarbonyl, aminocarbonylalkyl, and aminocarbonylamino, and each of said amino groups is optionally monosubstituted or disubstituted with alkyl, or is contained in a pyrrolidinyl, piperidinyl, morpholinyl, or piperazinyl group.

41. The compound of claim 27, wherein $R^1$ is —NR^aR^b; $R^a$ is selected from the group consisting of hydrogen, C_{1-9} alkyl, and C_{1-6} alkoxyalkyl; and $R^b$ is selected from the group consisting of C_{1-9} alkyl, hydroxyalkyl, C_{1-6} alkoxyalkyl, C_{3-6} cycloalkyl-C_{1-3} alkyl, heterocyclylalkyl, arylalkyl, and heteroarylalkyl.

42. The compound of claim 27 wherein
$R^1$ is —CR^cR^dR^e;
$R^c$ is —NR^{a'''}R^{b'''};
$R^d$ and $R^e$ are each independently selected from the group consisting of hydrogen and C_{1-9}alkyl;
$R^{a'''}$ is selected from the group consisting of hydrogen, C_{1-9} alkyl, and C_{1-6} alkoxyalkyl; and
$R^{b'''}$ is selected from the group consisting of C_{1-9} alkyl, hydroxyalkyl, C_{1-6} alkoxyalkyl, C_{3-6} cycloalkyl-C_{1-3} alkyl, heterocyclylalkyl, arylalkyl, and heteroarylalkyl, wherein each of said aryl or heteroaryl groups is optionally substituted.

43. The compound of claim 27, wherein $R^1$ is aryl or heteroaryl where said aryl or heteroaryl is optionally substituted.

44. The compound of claim 43, where said aryl or heteroaryl is optionally substituted with one or more substituents independently selected from C_{1-6} alkyl, C_{1-6} alkoxy, halogen, haloalkyl, cyano, and —NR^{a'}R^{b'}, where $R^{a'}$ and $R^{b'}$ are each independently selected from the group consisting of hydrogen, C_{1-9} alkyl, and C_{1-9} alkylcarbonyl.

45. A pharmaceutical composition comprising a therapeutically effective amount of at least one compound of formula I

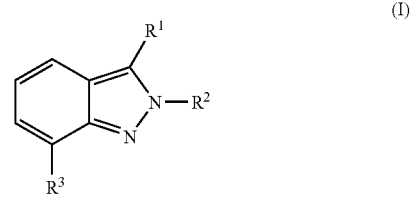

(I)

wherein:
$R^1$ is —NR^aR^b, —CR^cR^dR^e, CO_2R^a, or —C(O)NR^aR^b; or $R^1$ is cycloalkenyl, aryl, or heteroaryl, where each aryl or heteroaryl is optionally substituted with one or more substituents independently selected from C_{1-6} alkyl, C_{1-6} alkoxy, C_{1-6} alkylthio, C_{1-6} alkylsulfonyl, halogen, haloalkyl, cyano, nitro, —C(O)NR^{a'}R^{b'}, and —NR^{a'}R^{b'}, where $R^{a'\,and\,R^{b'}}$ are each independently selected from the group consisting of hydrogen, C_{1-9} alkyl, and C_{1-9} alkylcarbonyl; and with the proviso that $R^1$ can not be 4-methoxyphenyl when $R^3$ is unsusbtituted phenyl;

$R^2$ is hydrogen, C_{1-6} alkyl, C_{3-6} cycloalkyl, C_{3-6} cycloalkyl-C_{1-3} alkyl, C_{1-6} alkylcarbonyl, C_{1-6} alkylsulfonyl, aryl, or arylalkyl, wherein said aryl or arylalkyl is optionally substituted with one or more substituents independently selected from C_{1-6} alkyl, haloalkyl, C_{1-6} alkoxy, and halogen;

$R^3$ is aryl or heteroaryl, each optionally substituted with one or more substituents independently selected from the group consisting of C_{1-6} alkyl, C_{1-6} alkoxy, C_{1-6} alkylthio, C_{1-6} alkylsulfonyl, aminosulfonyl, monoalkylaminosulfonyl, dialkylaminosulfonyl, halogen, haloalkyl, cyano, nitro, and —NR^{a''}R^{b''}, where $R^{a''}$ and $R^{b''}$ are each independently selected from the group consisting of hydrogen, C_{1-9} alkyl, and C_{1-9} alkylcarbonyl;

$R^a$ and $R^b$ are each independently selected from the group consisting of hydrogen, C_{1-9} alkyl, hydroxyalkyl, C_{1-6} alkoxyalkyl, C_{1-6} alkylthioalkyl, carboxyalkyl, acyl, C_{3-6} cycloalkyl, C_{3-6} cycloalkyl-C_{1-3} alkyl, di-C_{3-6} cycloalkylC_{1-3} alkyl, C_{1-6} heteroalkyl, aminoalkyl, aminocarbonylalkyl, cyanoalkyl, C_{5-8} heterocyclyl, heterocyclylalkyl, aryl, arylalkyl, heteroaryl, heteroarylalkyl, phenylalkyl, diphenylalkyl, and C_{1-3} alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or $R^a$ and $R^b$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylaminio, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$ alkyl, haloalkyl, $C_{1-6}$ alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group pyrrolidin-1-yl, piperidin-1-yl, morpholin-1-yl and piperazin-1-yl;

$R^c$ is hydrogen, hydroxy, $C_{1-6}$ alkoxy, or $-NR^{a'''}R^{b'''}$;

$R^d$ and $R^e$ are each independently selected from the group consisting of hydrogen, $C_{1-9}$ alkyl, hydroxyalkyl, $C_{1-6}$ alkoxyalkyl, $C_{1-6}$ alkylthioalkyl, heteroalkyl, heterocyclyl, heterocyclylalkyl, $C_{3-6}$ cycloalkyl, $C_{3-6}$ cycloalkyl-$C_{1-3}$ alkyl, di-$C_{3-6}$ cycloalkyl-$C_{1-3}$ alkyl, aryl, arylalkyl, heteroaryl, heteroarylalkyl, phenylalkyl, diphenyl-$C_{1-3}$alkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, and halogen; or $R^c$ and $R^d$ are taken together to form a divalent group selected from $C_{1-6}$ alkylidenyl, $C_{1-6}$ heteroalkylidenyl, $C_{3-6}$ cycloalkylidenyl, $C_{3-6}$ cycloalkyl-alkylidenyl, $C_{3-6}$ cycloalkyl-$C_{1-3}$ alkyl-alkylidenyl, $C_{3-6}$ heterocyclylidenyl, $C_{3-6}$ heterocyclyl-$C_{1-3}$ alkylidenyl, $C_{3-6}$ heterocyclylalkyl-$C_{1-3}$ alkylidenyl, aryl-$C_{1-3}$ alkylidenyl, aryl-$C_{1-3}$alkyl-alkylidenyl, heteroaryl-$C_{1-3}$alkylidenyl, and heteroarylalkyl-Cl -3 alkylidenyl, wherein each of said cycloalkyl, aryl, or heteroaryl groups is optionally substituted with one or more substituents independently selected from $C_{1-6}$ alkyl, haloalkyl, $C_{1-6}$ alkoxy, amino, alkylamino, dialkylamino, and halogen; or $R^d$ and $R^e$ are taken together with the carbon to which they are attached to form a cycloalkyl or heterocyclyl ring;

$R^{a''}$ and $R^{b'''}$ are each independently selected from the group consisting of hydrogen, $C_{1-9}$ alkyl, hydroxyalkyl, $C_{1-6}$ alkoxyalkyl, $C_{1-6}$ alkylthioalkyl, carboxyalkyl, acyl, $C_{3-6}$ cycloalkyl, $C_{3-6}$ cycloalkyl-$C_{1-3}$ alkyl, di-$C_{3-6}$ cycloalkyl-$C_{1-3}$ alkyl, $C_{1-6}$ heteroalkyl, aminoalkyl, aminocarbonylalkyl, cyanoalkyl, $C_{5-8}$ heterocyclyl, heterocyclylalkyl, aryl, arylalkyl, heteroaryl, heteroarylalkyl, phenylalkyl, diphenyl-$C_{1-3}$ alkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or $R^{a'''}$ and $R^{b'''}$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$alkyl, haloalkyl, $C_{1-6}$alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group;

or individual stereoisomers, racemic or non-racemic mixtures of stereoisomers, or pharmaceutically acceptable salts thereof; in admixture with at least one pharmaceutically acceptable carrier.

* * * * *